United States Patent [19]

Macias et al.

[11] 4,356,818
[45] Nov. 2, 1982

[54] DIAPER WITH MOISTURE DETECTING APPARATUS

[76] Inventors: Helene Macias; Angos Winke, both of 5333 Russell Ave., Suite 301, Hollywood, Calif. 90027

[21] Appl. No.: 99,641

[22] Filed: Dec. 3, 1979

[51] Int. Cl.³ .................. A61B 19/00; A61F 13/16
[52] U.S. Cl. ...................... 128/138 A; 128/284; 128/287
[58] Field of Search ............... 128/284, 287, 138 A

[56] References Cited

U.S. PATENT DOCUMENTS

| | | | |
|---|---|---|---|
| 1,749,826 | 3/1930 | Lubach | 128/138 A |
| 3,460,123 | 8/1969 | Bass | 128/138 A |
| 3,508,235 | 4/1970 | Baisden | 128/138 A |
| 3,759,246 | 9/1973 | Flack et al. | 128/138 A |
| 4,040,423 | 8/1977 | Jones, Sr. | 128/287 |
| 4,106,001 | 8/1979 | Mahoney | 128/138 A |
| 4,163,449 | 8/1979 | Regal | 128/138 A |
| 4,191,950 | 3/1980 | Levin et al. | 128/138 A |
| 4,212,295 | 7/1980 | Snyder | 128/138 A |

Primary Examiner—V. Millin
Assistant Examiner—C. W. Shedd

[57] ABSTRACT

In general, the preferred form of the present invention comprises an electrical moisture sensing disposable baby diaper, having a moisture or liquid impervious outer sheet and a superimposed liquid permeable inner lining encapsulating a moisture absorbent wadding, and one single continuous electrically conductive material or two thin electrically conductive materials affixed flatly to one opposing surface between the outer sheet and the inner lining in an arrangement wherein a cavity comprising the feature of the touching of opposite inside surfaces is adjoined with one or more discrete securing means located within the central area respective the exterior margin of the absorbent wadding layer to provide a first and a second length of conduit of circuitry in said cavity respective the electrically conductive material, therefore to communicate with the inner lining and in the presence of moisture electrically short circuiting the electrically conductive materials, immediately signal the wet condition of the inner lining to an electrical alarm device appropriately connected to the electrically conductive materials. A second type of diaper of our invention includes an antenna of a separate electrically conductive material similarly affixed flatly to one surface of a conduit supporting sheet, to radiate to a distant wireless indicator the output of an electrical alarm device appropriately connected to the antenna and the electrically conductive materials. Physical separation of the electrically conductive materials, and the outer sheet to lining positioning arrangement within the diaper, is maintained by directly bonding together at one or more intervals, small portions of the various proximate and opposite surfaces of the outer sheet and the inner lining disposed central of the distance that one length of conductor is laterally removed from a similar length, or extending across, the individual electrically conductive materials, therefore to allow moisture or wetness to easily permeate around and between adjacent bonded portions of the inner lining, and across and throughout the absorbant material.

A third type of diaper of our invention includes an antenna of a separate electrically conductive material similarly affixed flatly to one of the surfaces of a conduit supporting sheet to radiate to a distant wireless indicator of an electrical alarm device appropriately connected to the antenna and the electrically conductive materials.

137 Claims, 20 Drawing Figures

DIAPER WITH MOISTURE DETECTING APPARATUS

BACKGROUND OF THE INVENTION

This invention relates to throw-away diapers or washable diapers which have incorporated in them or attached to them electrical signal means which will immediately give an audible or visual signal that the baby's diaper is wet.

Baby diaper rash is for the nursing mother the most enigmatic problem of infant rearing, and although the caring mother bears an emotional burden when hearing her baby cry, it is the baby who actually suffers pain and an acute experience of trauma, the cumulative effects of which during the first years after birth, as perceived by the young and impressionable subconscious mind, many psychologists suggest, is the prime neonatal originator of psychotic behavior that during later periods of the baby's life is the underlying case of an antisocial demeanor as developed and aggressively executed by many individuals towards fellow people.

In attempts to rid the basic dermis irritant, urine, from affecting the baby's skin, mothers often adhere to a strict, change of diaper, schedule. Although admittedly helpful, no real lessening of time wherein urine contacts with baby's skin is realized, because no prescribed timetable can fully anticipate an individual baby's changeable physical constitution. Frequently, a baby will micturate immediately after a change of diaper, and thus, unbeknown to the mother, be left to wallow in a soiled diaper until the next scheduled change of diaper, since until now a mother has had no way of knowing precisely when her baby has micturated, and consequently when her baby's diaper needed to be changed. The cliché spoken by a mother when her baby cries, in that "baby must be wet", clearly confirms that the mother has failed in her attempt to keep her baby dry, and free of baby diaper rash causing irritants, and that she therefore needs this present invention.

Previous inventions relating to human body fluid detecting devices have in the past only been directed towards meeting the brief requirements of subjects like children of higher age groups which were in need of an electrical alarm device to temporarily assist in training to overcome chronic bed wetting.

Of numerous prior systems, some are accessories to be placed between layers of bedding as indicated in U.S. Pat. Nos. 2,687,721, 2,812,757, 2,866,454, 2,907,841, while others are to be either temporarily secured to a garment as indicated in U.S. Pat. No. 3,530,855, or placed within the vacant space between the subject and the surrounding garment as indicated in U.S. Pat. Nos. 2,874,695, 3,441,019, 3,696,357, 3,864,676, 3,809,079, while another system is indicated in U.S. Pat. No. 3,460,123, wherein two wire mesh screens in a superimposed relation with a liquid permeable, electrical insulator between them, are permanently secured to a limited area of the crotch portion of an expensive and reusable tailored "jockey shorts" style undergarment, (a configuration similar in feature to a system indicated in U.S. Pat. No. 2,866,454, and not at all like in the present invention.)

Unfortunately, systems which are placed under layers of bedding or are placed outside of the gown of a patient or upon the seat of perhaps a wheel-chair are not suitable for use with babies in diapers, in that the diaper surrounding the baby, absorbs the escaping urine and thus prevents the released urine, from flowing onto the layers of bedding, and permeate through the material to cause an electrical short circuit across the switch terminals of an alarm circuit, which being normally open, would now become closed and thereby actuate an alarm. Moreover, the systems indicated in U.S. Pat. Nos. 2,687,721, 3,759,246, in particular are prone to signaling false alarms when creased and wrinkled, since the electrically conductive threads or strips, which are respectively sewn or painted on the sheet of absorptive material, are free and unrestricted to physically contact with each other and thereby, in the absence of moisture, electrically short circuit together when the material is crushed by a subject moving about thereupon.

Furthermore, by reason that modern throw-away baby diapers structurally include an electrically non-conductive, plastic-like outside covering to contain absorbed moisture within the fibers of the inner wadding material and away from outside of the diaper, systems as indicated in U.S. Pat. Nos. 3,530,855, 4,106,001, where either electrode sensors may be secured to either side of a garment so that moisture permeating from the inner surface of the material to the outside surface of the same material electrically short circuits the electrodes together, or, where the electrodes are affixed to the outside surface of garment material, cease to electrically function when attached to modern structured throw-away diapers.

Other moisture indicating devices illustrated in U.S. Pat. Nos. 2,874,695, 3,441,019, 3,696,357, 3,864,676, 3,809,079, 4,191,950 relate to diapers as an auxiliary appurtenance rather than to genuinely integrated electrical micturition detecting throw-away baby diapers, and thus share in various limitations imposed by their very conceptions. Wherein Vaniman teaches of electrode incorporation into washable napkin arrangements which snap fasten to a body encircling belt, so to prevent the napkin from working its way out from between the user and the apart diaper, the complex stages of inter-napkin electrode constructions indicated, fail to realize systems suitable for use in high-speed disposable diaper mass-manufacturing. Referring to the Kilgore, Mozes and Macias' devices, it must be noted that those and similar aparatus require a few drops of urine fluid applied directly thereupon to function. Whereas linen diapers incur a momentary puddling condition during micturition thereby assisting the functioning of these electrical devices and obviating the need for critical positioning within the crotch, no such incident of fluid collection occurs within composite disposable diapers, as the included hydrophobic inner lining rapidly conducts escaping urine unidirectionally therethrough and over the entire surface area thereof, for example, as shown in U.S. Pat. No. 3,180,335, thus drawing away from the source of micturition and towards the outer sheet, the necessary drops of urine required to operate these separately sheathed and independent electrical devices in a constant and reliable manner. Also, previous systems which include a radio transmitter-receiver link to connect sections of an alarm as indicated in U.S. Pat. No. 3,460,123, have failed to realize a construction suitable to radiate an alarm signal, and thus may interfere with baby's movements, operate unreliably over a limited range, or not at all, and are therefore substantially ineffectual. Therefore, the objects of these and other past systems adapted for portable use, all similarly lack in anticipatory teachings of desirable combinations of elements and features which would provide a suitable system directed towards the specialized needs in neonatal hygiene practice; and have failed to become commercialized or achieved any success in the market place.

SUMMARY OF THE INVENTION

Our invention provides a washable or throw-away diaper which can be handled and used just like the ordinary diapers which are on the market today; but will have within or associated with them signal means and in certain forms an antenna means which give visible or audible signals when the diaper becomes wet. The diaper is provided with flexible lateral spaced electrical conductors which extend across the diaper either diagonally or longitudinally or in combination and which are out of contact with the baby so that the baby will never experience an electrical shock. The conductors project from an edge of the diaper and are connected into the circuitry of a signal means of the general type shown in our earlier U.S. Pat. No. 3,864,676 issued Feb. 4, 1975, which may alternately incorporate a liquid crystal display as indicator device or be associated with means wherein a wireless receiver is adapted to be responsive, only to radiated signals of appropriate codes as conditioned by companion code generators contained within the circuitry of said signal means.

It is an object of our invention to provide a diaper which has incorporated in it conductors of a signal means, these conductors being embodied in the diaper at a minimum of cost, so that the cost of obtaining a diaper having the features of our invention will not be a price factor.

It is an object of our invention to provide the conduits of circuitry means of the signaling system either when the diaper is manufactured or added to the diaper by the mother when the diaper is applied.

It is an object of our invention to provide a diaper of the class described in which the second conductor is removed a lateral distance from the first conductor, said conductors held in place in this separated position so that they will not accidentally contact each other and thus give a false signal; and to provide an arrangement in which there is incorporated in the absorbent material of the diaper one or more annular absorbency paths flow paths from one conduit of circuitry to the other whereby moisture of the wetted diaper may more quickly electrically short circuit the conductors and operate the signal.

It is an object of our invention to provide in or for a diaper of the class described conduit-supporting sheet means which hold the second conductor a lateral distance removed from the first conductor and which may be applied to the inner surface of the washable or throw-away diaper, the diaper having sheets on each side of the absorbent layer, which sheets may be non-absorbing and excreta-transmitting or may constitute a sheet through which liquid cannot flow.

It is another object of our invention to provide a diaper of the class described in which, within a median location respective the edges of said absorbent wadding, encapsulated, between said inner sheet and said backing sheet comprising the diaper, one or more discrete portions of proximate and adjacent surfaces located at the distance said second conductor is removed from said first conductor are secured to the absorbent sheet either adhesively or by heat or otherwise and which serves as a means for providing a first and a second conduit of circuitry at the common means comprising the touching of sheets not adjoined at the distance said second conductor is removed from said first conductor and preventing the conductors from contacting each other and also a means for providing one or more of the annular absorbency paths referred to heretofore.

Manufactured diapers usually have an inner absorbent sheet which is relatively fluffy and flexible in combination with one or more outer sheets, one which is moisture transmitting and the other of which on the opposite side is moisture impervious. It is an object of our invention to provide the impervious outer sheet with the conductor means or an antenna means previously referred to which constitutes the only additional step in manufacturing the diaper. The applying of the various conductors may be very easily, quickly and cheaply incorporated in the diaper. The conductors may be separate, very thin strips of any electrical conductive material such as a very thin vacuum disposited foil or the conduits may be separate, very thin strips of any electrical conductive elastic such as a tacky electrically conducting adhesive, one single continuous conduit means, or the conduits may be provided by using an electrically conducting polymer on the surface of the outer sheet of the diaper, the polymer being applied in one or more strips and acting as the conductor means and antenna means of the diaper.

Another object of our invention is to provide an electrical conductor assembly consisting of a relatively narrow flexible strap on which the electrical conductors have previously been applied. In the assembly of the diaper parts this flexible strip is merely secured in the diaper between the inner sheet and outer sheet and the cost of so doing is only the cost of the flexible strip and conductors, the feeding of the strips into the diapers being merely a part of the functioning of the diaper assembling machine.

It is an object of our invention to provide the diaper of our invention with a feature which will assist the blind mother with type of digestion recognition by providing two parallel electrical conductors wherein at least one of the conductive means has marked resistance to electrical conductivity so that therewith connected electrical measurement and signaling circuitry can indicate the location of diaper soilage. Moisture deposited farther away from the connected signal measurement means will provide across the conduits a measured electrical resistance of greater magnitude than if the moisture were deposited close to the connected measurement means.

It is also an object of our invention to provide a diaper having signaling means in which the diaper includes antenna means which radiates a signal to a receiver and thus eliminates wiring which extends from the diaper and connected signaling device and thus eliminates the possibility of the baby being entangled in a loose wire or wires.

It is a further object of our invention for the blind mother to provide a single electrical conductor suitable for digestion identification consisting of two spaced apart conductor means of reduced electrical conductivity which are adjoined at one opposite end to provide one single continuous electrical conductor.

It is an object of our invention to assist the blind mother to provide means which may be integral with or may be affixed to the ends of spaced apart conductor means opposite the conductor ends which connect into the circuitry of a signal means.

It is another object of our invention to provide a diaper which has external marking means indicating to the diaper user the exact lateral distance of the electrical conductors which are within the diaper.

It is a still further object of our invention to provide a unique means for incorporating the conduits within the diaper without any danger of the conductors electrically short-circuiting. This object of our invention is accomplished by placing the conductors on opposite sides of a sheet of material which may constitute part of the diaper or may constitute a separate sheet to be added to the diaper when the mother applies the diaper to the baby. By making two folds in the supporting sheet, the conduits will be placed on opposite sides of the material in a relatively close parallel relationship.

It is a still further object of our invention to provide a diaper of our invention in which the electrical conductors themselves form an antenna.

It is a further object to provide said strip with tactile ability which directs moisture from proximate materials to the strip by providing the two sides of the strip with a flocking of fluffy wadding which is affixed to the strip by means of a porous adhesive provided on each side of the strip.

It is an additional object of our invention to provide in a diaper of the class described a moisture delaying or retarding means to protect against the the conductors electrically short circuiting by a negligible amount of moisture, such as would occur from perspiring, in order to prevent false or erroneous signals.

BRIEF DESCRIPTION OF THE DRAWINGS

Referring to the drawings.

DESCRIPTION OF THE PREFERRED EMBODIMENTS

Figure 1:
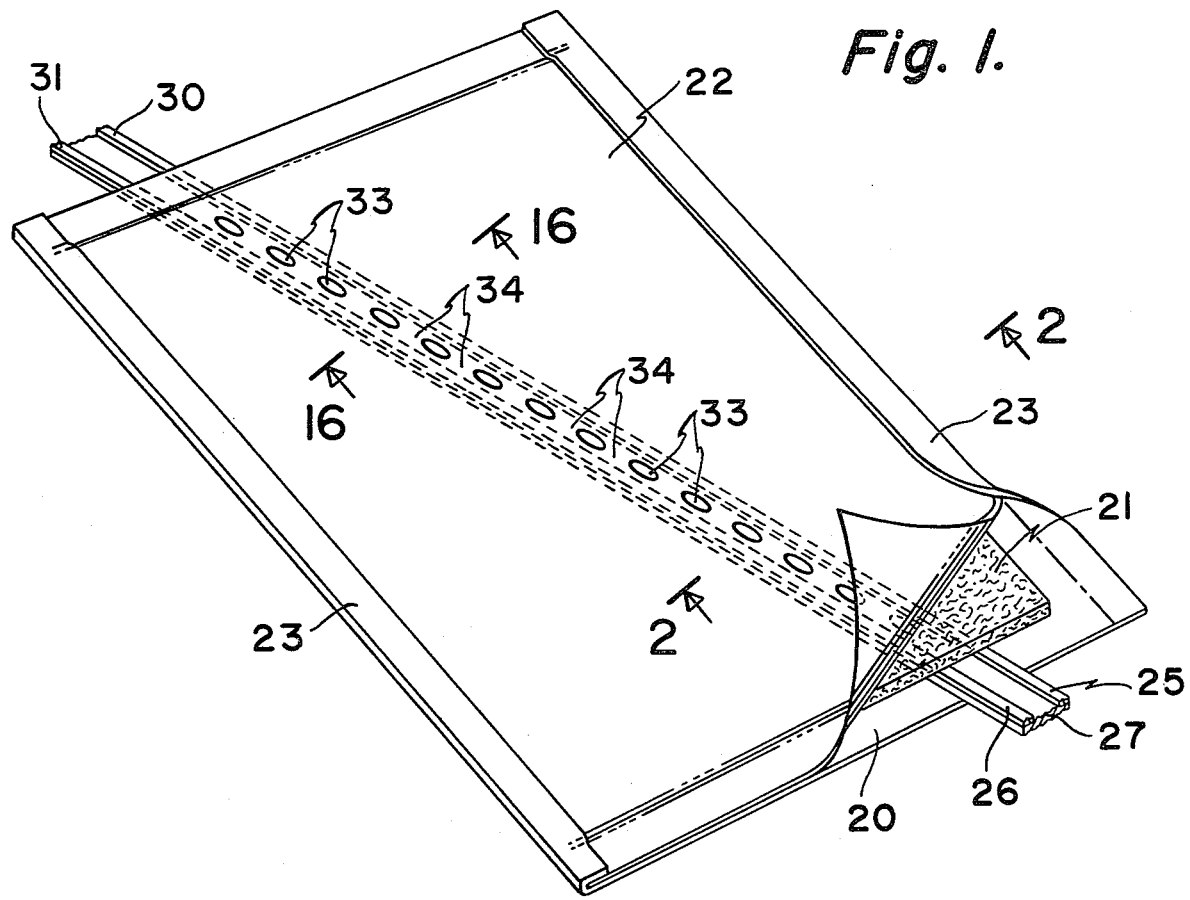
FIG. 1 is a perspective view illustrating a diaper of our invention in which the electrical conductors are applied to a flexible strip and the flexible strip is positioned between the flexible backing sheet and the absorbent material and secured by one or more tufting means located within a median location respective the edges of the absorbent material shown encapsulated between the moisture impervious backing sheet and the non-absorbing moisture permeable inner sheet.
Figure 2:
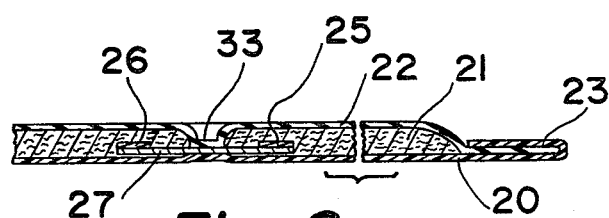
FIG. 2 is a sectional view of one form of dimple or tufting means providing one form of a first and a second conduit of circuitry at the common touching comprising the portions of common surfaces not adjoined through the axis of the dimple means further disclosing at said touching one form of providing a second conductor removed from a first conductor taken along the line 2—2 of FIG. 1 and illustrating furthermore the absorbent material formed by the presence of one or more tufting means to provide in the absorbent material annular drainage path means around the tuft from one conduit of circuitry to the other.

Referring to the form of the invention shown in FIGS. 1 and 2, the numeral 20 is a moisture impervious backing sheet which may be made out of a plastic or flexible material which has the characteristics of being readily folded and being impervious to moisture. Positioned adjacent to the backing sheet 20 is an absorbent layer 21 which absorbs the baby's urine. This sheet is of a material common in the trade and used in disposable diapers. 22 is a porous non-absorbing sheet which is applied to the inner surface of the moisture-absorbing layer 21. This sheet has the characteristic of allowing the urine to flow therethrough without retaining any of the urine therein with the result that an attempt is made to prevent the urine from continually or continuously contacting the baby. This sheet is held in place by having its edges positioned within the fold 23 of the backing sheet 20. Positioned with the diaper are the twin conductors which form a part of the circuitry of the signaling means as shown in FIGS. 1 and 2. The conductors 25 and 26 are secured to a flexible strip 27 which is positioned between a common touching comprising the backing sheet 20 and the absorbent layer 21. The strip 27 is secured to the backing sheet 20 in any suitable way such as gluing or by a heat process and the ends 30 and 31 project from the diaper and can be connected to the circuitry of the signaling device. The diaper in use, of course, may be folded or wrinkled and it would be possible for the two conductors to contact each other, electrically short circuit the circuitry and give a false signal. To prevent this from occurring, we apply or form one or more tuftings or depressions 33 in the inner sheet 22 or even in the backing sheet 20, and these depressed or dimpled portions 33 as shown in FIG. 2 may touch the strip 27. These dimple depressed portions may be adjoined by electrically operated disposable diaper adjoining means known in the trade as heat sealing, ultra-sonic belly-button or plug insertion riveting, or even by adhesive or bonding with the other parts so that they are kept in their depressed shape. These areas 33 are discrete located within a median location respective the edges of the absorbent material as shown in FIG. 1 to provide annular drainage means comprising absorbency spaces or paths 34 around and between one or more discrete dimpled portions 33 for the communication of moisture from one of the conductors 25 or 26 to the other of the conductors in order that the urine moisture may readily travel throughout the absorbent material 21 by permeating between the depressions 33 and thus wet the intervening absorbent material through the pathway 34 which is occupied by the absorbent material.

Figure 1A:
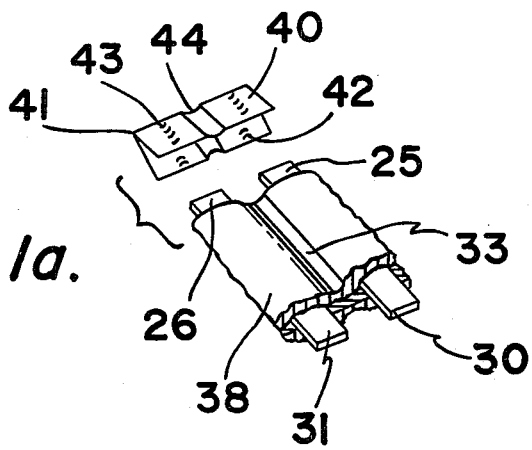
FIG. 1a illustrates a fragmentary view of a diaper showing a modified form of conductor means in which there is but one single circuitry member having two parts.

If desired, other electrical configurations for conductors 25 and 26 can easily be provided by replacing at least one of the two conductors with an altered conductor that is of dissimilar electrical resistance or perhaps both conductors 25 and 26 may be altered to provide an increased electrical resistance along at least one portion of length. An alternate arrangement provides one single continuous conductor to communicate of moisture issuing from the baby to a connected signal means wherein a first conductor 25 extending from one edge to an opposite edge of a diaper is electrically adjoined with a second conductor 26 which extends back to the beginning of the first conductor. In other words, having the appearance of a horseshoe. Thus, we now have one continuous conductor or circuit which has two parts 30 and 31. Broadly, the parts 30 and 31 comprise one conductor means. FIG. 1a demonstrates a separate section 40 provided with an electrically conducting material which is easily bent upon itself along crease 41 so as to allow affixing to the ends of conductors 30, 31 and the edge of depressed portion 33. Conductor grippers 42 and 43 may be raised ridges or similar projections which prevent the section 40 from separating with the conductors. Dimple 44 aids in aligning the section 40 with the conductors by fitting into the depressed portion 33.

Figure 1B:
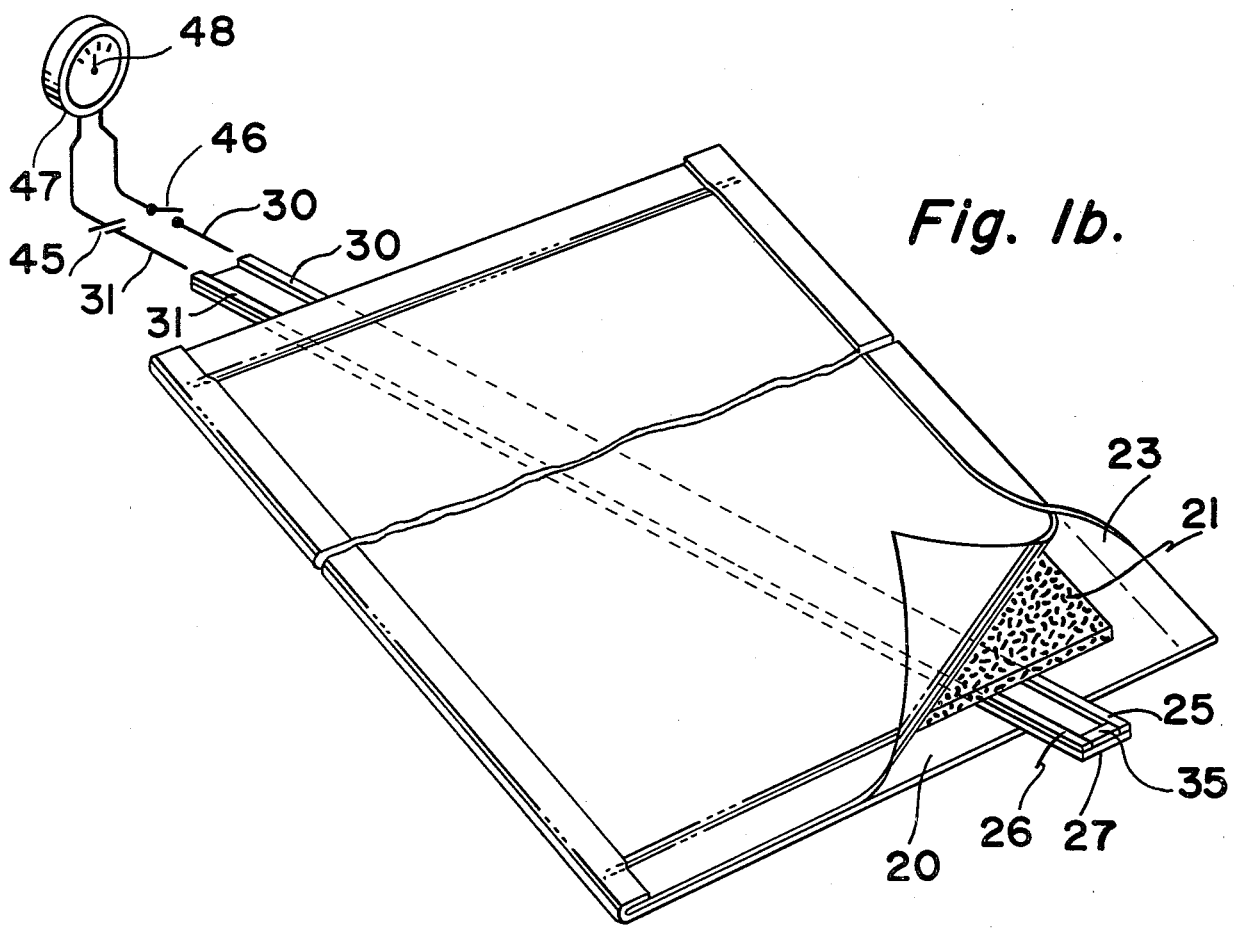
FIG. 1b illustrates a third form of conductor means.

FIG. 1b illustrates one continuous conductor arrangement wherein conductors 30 and 31 are electrically adjoined by the section 35 of a material similar to that provided for the conductors 30 and 31.

In the form of our invention having a single circuit which comprises one conductor means, the two sides of the circuit 30 and 31 include a battery 45 and a circuit opening for closing switch 46 whereby the circuit may be opened or closed. Also enclosed in the circuit is an indicator means, a possible combination of readily available elements comprising a meter 47 having a pointer 48 which indicates the amount or the voltage of the current flowing through the circuit. This meter varies in its distance from an appropriately provided indicator to the mean location within the diaper means in accordance with the position where the two portions of the conductor are electrically short circuited or in other words, how much resistive circuit is electrically short circuited by reason of the moisture bridging across the sides or parts 30 and 31. The position of the pointer 48 will indicate the exact spot in the diaper where the electrical short circuiting occurs and will thus indicate the position of deposit at which the diaper is soiled.

Figure 4:
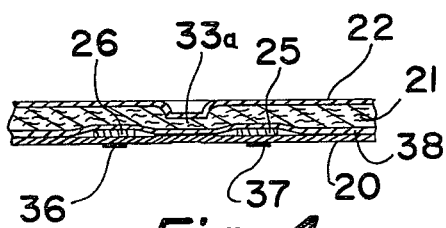
FIG. 4 is a sectional view taken on the line 4—4 of FIG. 3.
Figure 3:
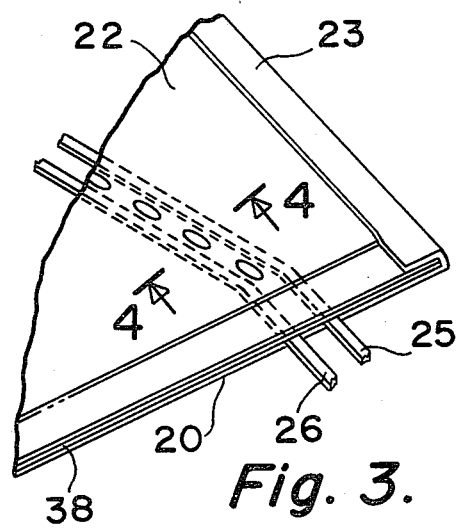
FIG. 3 is a fragmentary view of a corner of a diaper similar to that shown in FIGS. 1 and 2 but in which the flexible strip is eliminated and the two conductors are applied directly to the backing sheet.

In the form of our invention shown in FIGS. 3 and 4, the two conductors 25 and 26 are secured directly to the backing sheet 20. Also, in this form of the invention, there may be a moisture transmitting sheet 38 between the backing sheet and the absorbent layer 21. The parts are positioned as shown clearly in the cross-sectional view of FIG. 4. The length of a dimple or depression 33a across a portion of the diaper may be selected.

In this form of our invention, we show the indicating markings 36 and 37, which may be a strip of material or a painted strip on the outer surface of the backing sheet 20 which runs parallel to the conductors 25 and 26 so that the person applying the diaper will know exactly where the conductors are within the diaper.

Figure 5:
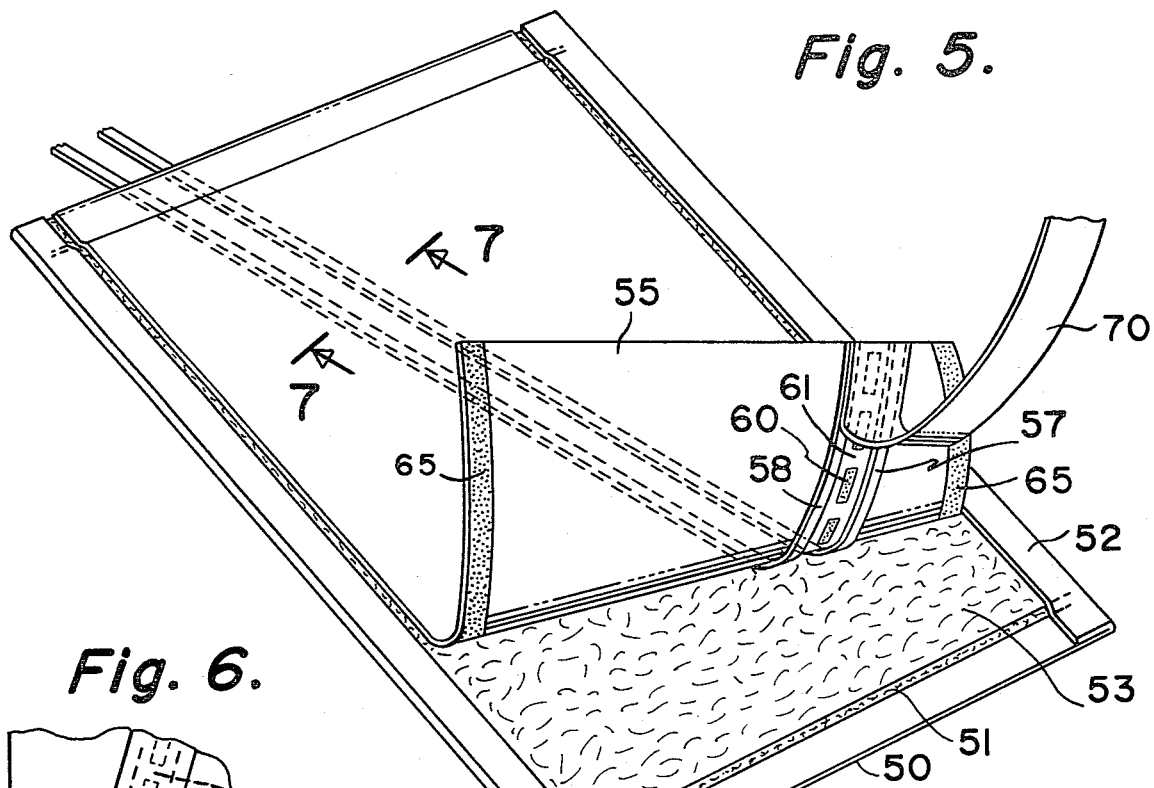
FIG. 5 is a perspective view of a diaper partly assembled in which a conductor supporting sheet is applied to the diaper, the conduits and one or more sheet tufting or dimpling means comprising prominenced sealing areas being formed on the sheet and these conductors and adhesive areas being protected by a removable strip which is removed at the time the conductor supporting sheet is applied to the diaper and incorporated as a part thereof.
Figure 6:
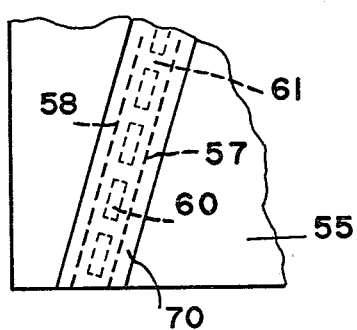
FIG. 6 is the fragmentary view of a corner of the diaper shown in FIG. 5.
Figure 7:
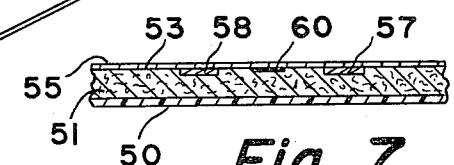
FIG. 7 is a fragmentary sectional view taken along the line 7—7 of FIG. 5.

Referring now to the form of our invention shown in FIGS. 5 to 7, the diaper shown therein is a throw-away diaper, but it should be understood that the diaper may be a washable diaper. As shown in the drawing, 50 is the outer plastic sheet and 51 is the absorbent layer. As shown, the edges of the plastic sheet are folded around the edges of the absorbent layer shown at 52. Used in conjunction with the diaper, which may be a washable diaper or a throw-away diaper, there is positioned against the upper surface 53 of the absorbent layer, a sheet 55 which as in the other forms of the invention is a liquid transmitting sheet but does not retain any wetness. Applied to this sheet, as is clearly shown in the folded back portion in FIG. 5, are two conductors 57 and 58 connected to the sheet 55 in any suitable way such as by glue or by heat. There conductors run parallel to each other and in the form of the invention shown in FIG. 5 the conductors run at an angle from one corner to an opposite corner of the diaper. Between the conductors is provided one or more sheet tufting means comprising discrete prominence areas 60 which may be adhesive areas or may in fact be a layer of the material which has an adhesive applied to it. Each discrete prominence 60 within a median location respective the absorbent layer 53 provides into the absorbent layer annular permeation passageways 61 so that moisture may flow in the absorbent layer 53 from one conductor to the other thus electrically short circuiting across and operating the signal. The conductor supporting sheet when applied to the surface of the absorbent layer 51 provides at the common touching a first and a second conduit of circuitry and is affixed thereto because of the adhesive areas or portions 60. Also, if desired, the longitudinal edges of the sheet 55 may be provided with adhesive 65 so that the longitudinal edges of the sheet will also be held in place.

As shown in FIG. 7, which is a cross-sectional view of FIG. 5, the layer or sheet 55 is positioned flatly against the layer 51 and may even be forced into the layer 51 as shown. The discrete tufting prevents the two conductors from being brought into contact with each other when the diaper is folded or wrinkled and this, of course, prevents inadvertent operation of the signal.

As previously stated, the conductor bearing sheet and the parts attached thereto may be incorporated as a part of the diaper, whether the diaper is a throw-away diaper or a washable diaper.

It is one of the objects of our invention to provide this type of sheet which can be applied by the mother to any standard throw-away or washable diaper when it is being put on the baby.

If we assume that FIG. 5 shows the conductor layer being installed in place, it will be seen that the sheet 55 in addition to having the conductors 57 and 58 and the prominence elements 60 also has a pull off cover strip or tape identified by the numeral 70. This strip is adhesively applied to the two conductors and covers the entire area so that the adhesive substance is covered and will not stick to anything. At the time the sheet 55 is applied, the cover strip 70 is removed as the sheet is being applied, and this is illustrated in FIG. 5 in which the strip 70 is almost completely removed. When the strip has been removed, then the portion of the sheet 55 which is bent upwardly is folded down and brought into contact with the surface of the layer of absorbent material identified by the numeral 53. The conductor supporting sheet may be provided in sheet form or may be provided in a roll and areas cut from the roll as needed, or the roll may have incorporated tear guides to dispense a pre-measured amount of material.

In FIGS. 8 to 11, we show a different method of applying the conductors to the supporting sheet. In this arrangement the conductors are applied to opposite sides of the conductor supporting sheet and therefore can never be brought into contact with each other, irrespective of wrinkling or folding, by reason of the fact that there is a layer of the supporting sheet material between the two conductors.

Figure 8:
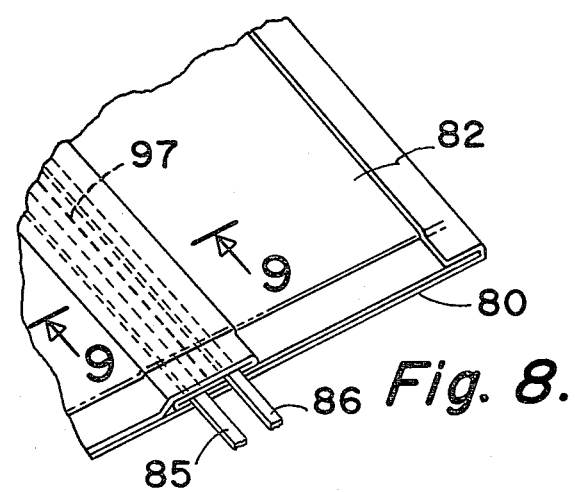
FIG. 8 is a fragmentary view of a diaper in which the conductors are positioned on a sheet which is a part of the diaper or which is applied to the diaper, the sheet being folded in order that the conductors will be on opposite sides of the sheet relatively close together and in which it is impossible for the conductors to come into contact with each other.
Figure 10:
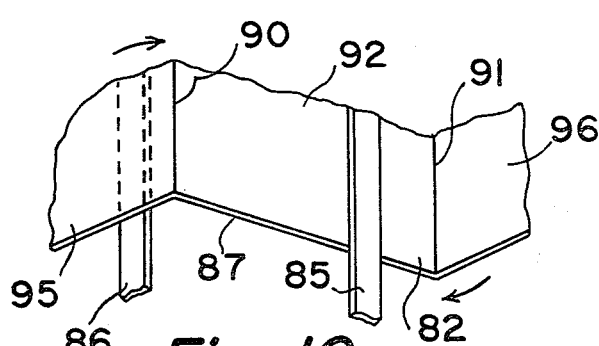
FIGS. 10 and 11 are views showing the supporting sheet for the conductors in the process of being folded in order to reach the position of the parts as shown in FIG. 8.
Figure 9:
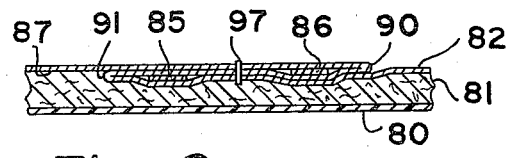
FIG. 9 is a sectional view taken on the line 9—9 of FIG. 8.
Figure 11:
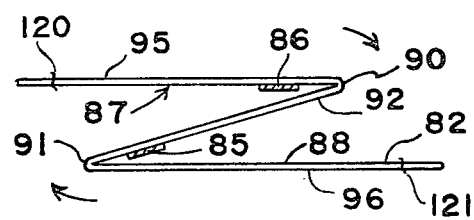

As shown in FIGS. 8 and 9, there is the backing sheet 80, the absorbent layer 81, and the conductor supporting sheet 82 which is a material which does not absorb moisture but allows the moisture to freely flow therethrough. Our invention provides two parallel conductors 85 and 86. The conductor 86 is applied to the top surface 87 of the sheet and the conductor 85 is connected to the lower surface of the sheet, the lower surface being indicated by the numeral 87. The sheet 82 is folded along the line 90 and 91 to provide a central panel 92. FIG. 10 shows the position of the parts at the commencement of the folding action and FIG. 10 shows the sheet and the position of the parts when the sheet is about two-thirds folded. It will be noted that the panel 92 is positioned between the edge parts 95 and 96, and in order to hold these parts in folded position, glue or other adhesive may be applied to the surfaces so that the sections of the sheet 82 will be secured in the position shown in FIG. 8. Also if desired, stitching 97 or perhaps distress welded construction may be used for this purpose. It will therefore be seen that irrespective of to what extent the diaper and the conductor supporting sheet may be wrinkled, bent or folded, the two conductors 85 and 86 can never come into contact with each other. In the form of the invention shown in FIGS. 8 to 10, the conductor supporting sheet is shown as being the upper sheet of the diaper.

Figure 12:
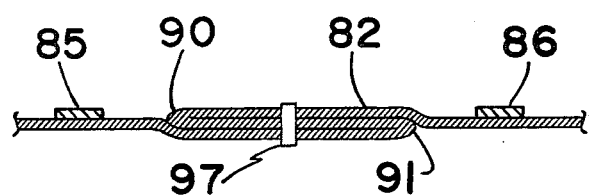
FIG. 12 is a modified form of the form of the invention shown in FIGS. 8 to 11, the supporting sheet being folded to provide a thickened, strengthened area at the distance between the two conductors.

In the form of our invention shown in FIG. 12, 85 and 86 are secured to the top surface of the sheet 82. The sheet 82 is folded at lines 90 and 91 to provide a folded and strengthened and thickened area between the two conductors 85 and 86. This central portion is thick enough and strong enough to prevent folding or wrinkling which might otherwise bring the conductors into unintended contact with each other. The folded portions may be secured together by any suitable means, such as stitching as shown at 97 or might even be glued together. Of course, the sheet 82 may be the backing sheet of the diaper and in this event the sheet 82 will be made out of a plastic non-porous material.

As shown in the various drawings the conductors may be adapted to one of the diaper elements or may be attached to a flexible strip which is in turn embodied or positioned within or connected to the diaper so as to become a part thereof.

In FIGS. 8 to 11 the flexible strip is shown as being an integral part of the layer 82. However, this particular flexible strip with the conductors therein may be provided as a separate element.

However, the flexible strip will be formed in the same way as it is formed as shown in FIGS. 8 to 10. When the flexible strip of this embodiment is used, it is made from a strip of material in which parallel edges of the strip end as indicated at 120 and 121 in FIG. 11. It will be noted that the strip is just wide enough to form the central layer 92 and the outer layers 95 and 96.

Figure 3A:
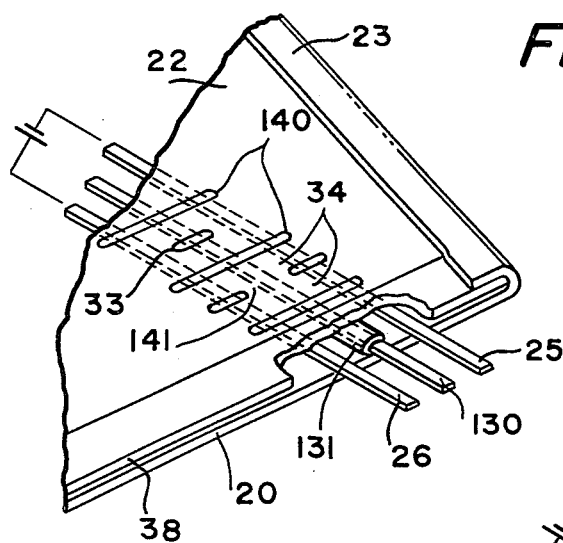
FIGS. 3a and 3b disclose two forms of our invention which has an antenna incorporated in the diaper.
Figure 3B:
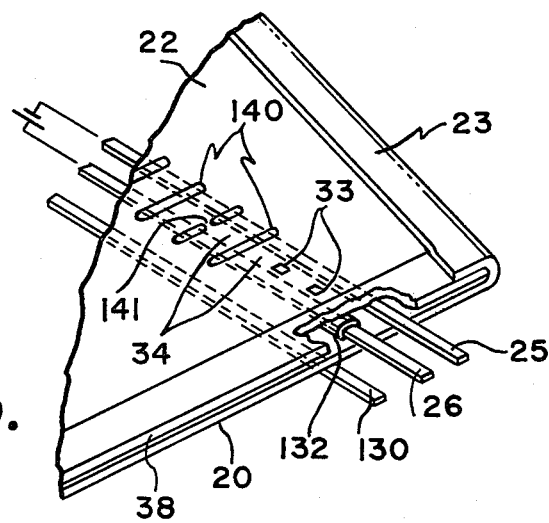

FIGS. 3a and 3b illustrate forms of our invention in which there is incorporated an antenna conductor 130 of a material similar to that of the conductors 25 and 26. The antenna 130 can be directly secured to the backing sheet 20. As stated heretofore, separate wires from the diaper to a signaling device are eliminated and this eliminates the danger of the baby being entangled with a loose wire. The antenna conductor 130 extends the full length or breadth of the diaper and therefore functions independently of the location where liquid electrically short circuits the two conductors 25 and 26.

Figure 13:
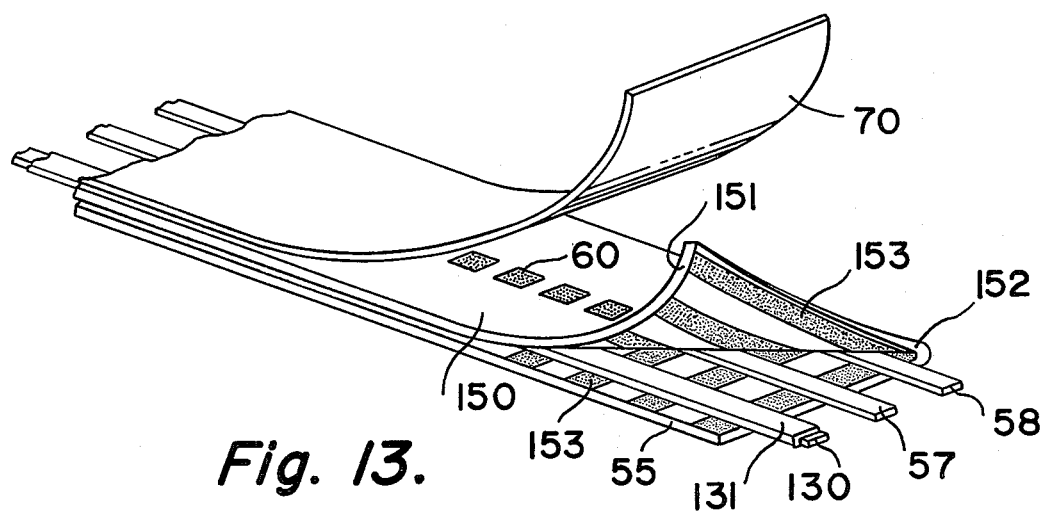
FIGS. 13 and 14 illustrate alternative forms of flexible strips having conductors which are provided as an integral part of a layer comprising a part of the diaper.

In the embodiment shown in FIG. 3a the antenna conductor 130 is positioned on the inner surface of the backing sheet 20 between the conductors 25 and 26. Where the antenna 130 requires to be isolated from interaction with liquid containing the conductors 25 and 26 a moisture barring film 131 of a silicon coating or other material can be provided to cover the entire length of the antenna. Alternately as shown in FIG. 3b the antenna conductor 130 may be secured to the outer surface of the backing sheet 20 and of course, when in such position, need not have the protective coating.

Where material selection requires an adjustment in response time in which the flow of liquid travels, from the conductor 25 across to conductor 26, the adjustment may be made by extending horizontal the depressed portions 33 as identified by numeral 140 to reach across the conductors 25 and 26 and by providing an opening 141 by means of a non-depressed portion at elected locations along the length of the depressed portion 140. As an alternative means of providing a delaying action, one of the conductors 25 or 26 may be provided with a coating of material 142 which may extend for the entire length of the conductor. This material may be a petroleum jelly which delays moisture reaching the conductor 25 or 26. An example of the utility of such means is where the conductors are highly sensitive to moisture and might be shorted by a small amount of moisture, such as perspiring, which would give an erroneous signal. The structure shown in FIG. 13 is a modified form of the invention shown in FIG. 5, and provides a novel conductor layer sheet 150 and a conductor cover sheet 151 from one single conductor bearing material 55 by virtue of one fold 152 in the conductor bearing material 55, thereby enabling the conductor bearing material 55 to be folded over upon itself, and the created conductor cover sheet 151 to be secured to the conductor layer sheet 150. The cover sheet 151 and the layer sheet 150 are secured together by means of an adhesive 153 applied to one side of the conductor bearing material 55, which one surface is common to each of the two sheets 150 and 151 when folded over. Retention of the conductors 57 and 58 and the optional antenna conductor 130 positioned in between the folded over conductor bearing material 55, is assured by the provided bonding means which tightly secures the two sheets 150 and 151 together. Wherein the present structure benefits equally well from the pull-off cover strip feature identified by the numeral 70 in FIG. 5, a similar feature is provided in the present structure as well as shown in FIG. 13 and therefore also identified by the same numeral. The adhesive elements 60 which are protected from inadvertent contacting with foreign matter prior to their being affixed to a diaper by the cover strip 70, are shown suitably provided on one outside surface of the sensor strip structure. The numeral 131 identifies an optional moisture barrier film or other barrier means provided for the length of antenna conductor 130.

Figure 14:
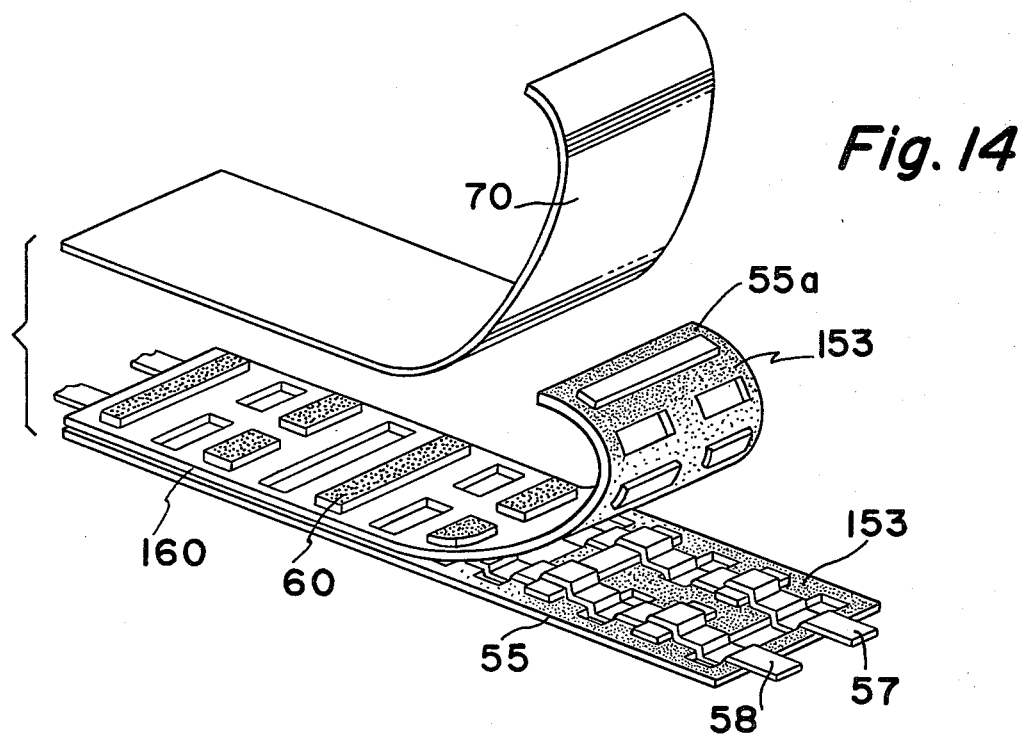
Figure 15:
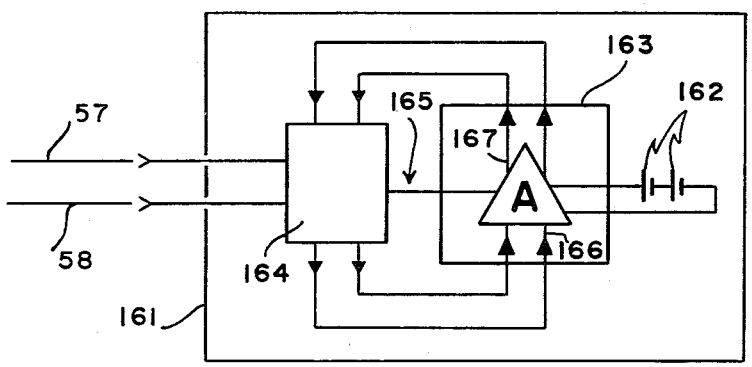
FIG. 15 is an electrical diagram in which the conductors provide antenna means when an appropriately connected alarm device responds to the signal of a soiled absorbent material.

FIG. 14 shows an alternate conductor supporting structure. This conductor bearing material is a modified form of the sheet illustrated in FIG. 5, and is particularly useful to the blind user in that the structure features a construction wherein either surface is the correct surface. In principle, the conductor supporting material 160 supports two electrical conductors 57 and 58, affixed between a first sheet 55 and a second sheet 55a, both sheets being of a flat and thin material, which are crushed together to form a corrugated patern. The two sheets 55 and 55a thus brought to form a corrugated pattern. The two sheets 55 and 55a thus brought to intimately embrace each other and forming one single conductor supporting material 160, thereby locking the two conductors 57 and 58 into position and prevent their displacement from between the two sheets 55 and 55a. If desired, as optional, adhesive or other binder means 153 can be provided to either or to both of the sheet surfaces which contacts with the other. As in previous structures, an adhesive material 60, can be provided on an outside surface of the structure and similarly protected by a removable cover strip 70.

Where no separate antenna conductor is used, the electrical conductors 57 and 58 can themselves provide the antenna conductor function, if, as shown in FIG. 15, an appropriately connected electrical alarm device 161 operated by a battery 162, connects the conductors 57 and 58 into appropriate alarm circuitry 163 that is provided with an electrically responsive switching means 164 whereby the alarm circuitry 163 signals 165 the switching means 164 to disconnect the conductors 57 and 58 from the electrical input 166 of the alarm device 161 and reconnect the conductors 57 and 58 to the electrical output 167 of the alarm device 161, after the conductors 57 and 58 have made the electrical input 166 of the alarm device 161 respond to the conductors 57 and 58.

Figure 16:
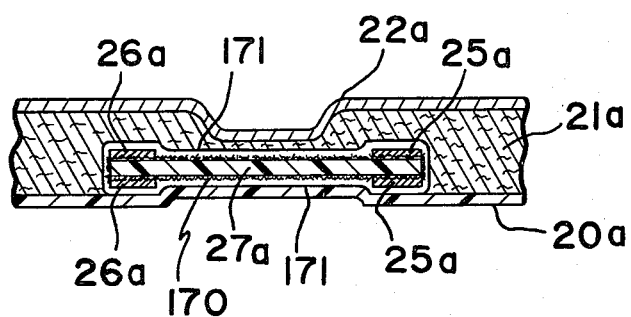
FIG. 16 is a view taken on line 16—16 of FIG. 1 clearly showing the backing sheet tufting or depression means and an alternative form of a flexible conductor supporting strip and parts associated therewith.

FIG. 16 shows a further alternative form of our invention. This view is a generally cross-sectional view taken in the position such as the line 16—16 of FIG. 1 which shows the conductor supporting strip and conductors of this further form of our invention. As shown in this view the conductor supporting strip which we have identified by the numeral 27a is provided with a porous adhesive coating 170 on opposite sides thereof. Conductors 25a and 26a are formed as shown by applying a flaky or granular current-conveying material along the edges which penetrates into the adhesive coating 170 and builds up thereon as shown. Thereafter a layer of moisture distributing flocking material 171 is provided around the entire assembly. This provides for a greater transfer of moisture across the surfaces of the strip 27a. This novel combination of our invention may be embodied in any one of the diapers comprising my invention and may therefore have the lower backing element 20a, material 21a and the top sheet 22a.

As obvious from the disclosure of the different embodiments of the invention, the separate strips or ribbons enclosing or supporting the conductors may be separately marketed and sold for embodiment by the user in any of the throw-away or washable diapers now on the market.

The term "wadding" as used in the abstract and in the claims broadly refers to any suitable moisture absorbent material, such as, for example, as is now used in throw-away diapers or cloth, washable diapers.

The term "support strip" as used in the claims refers to a strip such as shown in the various figures, which support strip supports the conductors and may either completely enclose the conductors as shown in FIG. 1a and FIGS. 8 and 9 or be positioned along one side thereof as shown in the other figures.

We claim:

1. In an absorbent wadding substantially dimensioned as a disposable diaper encapsulated between a moisture impervious backing sheet having an open surface and a non-absorbing moisture permeable inner sheet,
    the improvement of electrically sensing when said adsorbent wadding requires the disposal of a soiled diaper
    a. by providing said backing sheet one or more dimple depressing means to adjoin said securing means with said inner sheet and with said backing sheet within a median location respective the edges of said absorbent wadding,
    b. said dimple means defining flow paths to portions of said absorbent wadding not adjoined with said dimple means,
    c. said dimple means defining a first and a second longitudinal conduit of circuitry at the common touching comprising said absorbent wadding with backing sheet portions of said backing sheet not similarly adjoined with said dimple means,
    d. by providing a second conductor removed from a first conductor,
    e. said first and said second conductor arranged to extend across and affixed by securing means to the surface of said backing sheet facing said inner sheet characterized by
    f. a portion of said first conductor being common to said touching comprising said first longitudinal conduit of circuitry, and
    g. a portion of said second conductor being common to said touching comprising said second longitudinal conduit of circuitry
    thereby normally providing electrical isolation between said first and said second conductor and prevent contact between them when the diaper is folded or wrinkled, but allowing an electrical short circuit in the presence of electrically conductive digested fluid draining into said absorbent wadding.

2. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said backing sheet one or more depressed means within a median location respective the edges of said absorbent wadding, b. said depressed means being dimpled into said absorbent wadding by securing means to adjoin said inner sheet with said backing sheet, c. a portion of said absorbent wadding being adjoined with said securing means joining said inner sheet with said backing sheet, d. said securing means defining flow paths to portions of said absorbent wadding not adjoined with said secured dimple means, e. said securing means providing a first and a second longitudinal conduit of circuitry at the common touching comprising said absorbent wadding with backing sheet portions of said backing sheet not similarly adjoined with said dimple means, f. by providing a second conductor removed from a first conductor, g. said first and said second conductor arranged to extend across and affixed by securing means to the surface of said backing sheet facing said inner sheet characterized by h. a portion of said first conductor being common to said touching comprising said first longitudinal conduit of circuitry, and i. a portion of said second conductor being common to said touching comprising said second longitudinal conduit of circuitry thereby normally providing electrical isolation between said first and said second conductor and prevent contact between them when the diaper is folded or wrinkled, but allowing an electrical short circuit in the presence of electrically conductive digestive liquid draining into said absorbent wadding.

3. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said inner sheet one or more depressed means within a median location respective the edges of said absorbent wadding, b. said depressed means being dimpled into said absorbent wadding by securing means to adjoin said backing sheet with said inner sheet, c. a portion of said absorbent wadding being adjoined with said securing means joining said backing sheet with said inner sheet, d. said dimple means defining flow paths to portions of said absorbent wadding not adjoined with said secured dimple means, e. said dimple means providing a first and a second longitudinal conduit of circuitry at the common touching comprising said absorbent wadding with inner sheet portions of said inner sheet not similarly adjoined with said dimple means, f. by providing a second conductor removed from a first conductor, g. said first and said second conductor arranged to extend across and affixed by securing means to the surface of said inner sheet facing said backing sheet characterized by h. a portion of said first conductor being common to said touching comprising said first longitudinal conduit of circuitry, and i. a portion of said second conductor being common to said touching comprising said second longitudinal conduit of circuitry thereby normally providing electrical isolation between said first and said second conductor and prevent contact between them when the diaper is folded or wrinkled, but allowing an electrical short circuit in the presence of electrically conductive digested fluid voiding into said absorbent wadding.

4. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said inner sheet one strengthened and thickened longitudinal means within a median location respective the edges of said absorbent wadding, b. said strengthened and thickened means extending from a first edge to a second edge opposite said first edge, c. said strengthened and thickened means providing a first and a second longitudinal conduit of circuitry at the common touching comprising said absorbent wadding with inner sheet portions of said inner sheet not similarly provided with said strengthened and thickened means, d. by providing a second conductor removed from a first conductor, e. said first and said second conductor arranged to extend across and affixed by securing means to the surface of said inner sheet touching said absorbent wadding characterized by f. a portion of said first conductor being common to said touching comprising said first longitudinal conduit of circuitry, and g. a portion of said second conductor being common to said touching comprising said second longitudinal conduit of circuitry to provide a torsion resistant means at the distance said second conductor is removed from said first conductor to prevent contact between them when the diaper is folded or wrinkled, but allowing an electrical short circuit in the presence of electrically conductive digested moisture draining into said absorbent wadding.

5. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said inner sheet folded portions within a median location respective the edges of said absorbent wadding, b. said folded portions extending from a first edge to a second edge opposite said first edge, c. said folded portions comprising at least a first longitudinal fold, further folded away from said first fold back upon said first fold to define a second longitudinal fold, d. said folded portions of said inner sheet being affixed to itself with securing means to provide a first and a second longitudinal conduit of circuitry within said folded means not adjoined with said securing means, e. by providing a second conductor removed from a first conductor characterized by f. said first conductor arranged to extend across and affixed by securing means to the surface of said inner sheet touching said absorbent wadding, g. said second conductor arranged to extend across and affixed by securing means to the opposite surface of said inner sheet, and h. said first conductor being common to said first longitudinal conduit of circuitry, i. said second conductor being common to said second longitudinal conduit of circuitry, thereby providing electrical isolation between said first and said second conductor irrespective of the extent said inner sheet may be wrinkled, bent or folded, but allowing an electrical short circuit in the presence of electrically conductive digested moisture draining into said absorbent wadding.

6. An electrical moisture sensing means as defined in claim 5, wherein said first and said second longitudinal conduits of circuitry are enclosed.

7. An electrical moisture sensing means as defined in claim 5, in which the conductor supporting moisture permeable inner sheet is removably secured to the diaper.

8. A combination as defined in claim 7, in which a diaper comprises a disposable diaper characterized by an absorbent wadding layer substantially dimensioned as a diaper encapsulated between a moisture impervious backing sheet having an open surface and one or more liquid pervious inner sheets.

9. A combination as defined in claim 8, in which the flexible conductor supporting strip is affixed by securing means to other parts comprising a diaper.

10. A combination as defined in claim 9, in which securing means affix the flexible conductor supporting strip intermediate the parts comprising a diaper.

11. A combination as defined in claim 10, in which a diaper means provides securing means to affix the flexible conductor supporting strip.

12. A combination as defined in claim 9, in which means are provided for removably securing the flexible conductor supporting strip with other elements comprising a diaper.

13. A combination as defined in claim 5, in which said conductor supporting moisture permeable inner sheet comprises a flexible conductor supporting strip.

14. A combination as defined in claim 13, in which the parallel edges of said flexible conductor supporting strip securing said first and said second conductor end at said first and said second fold.

15. A combination as defined in claim 14, in which the flexible conductor supporting strip is an integral part of a layer of a diaper means.

16. An electrical moisture sensing diaper comprising in combination:

a. a moisture impervious backing sheet;

b. a layer of moisture absorbent wadding adjacent to and touching said backing sheet;

c. a non-absorbing moisture permeable inner sheet superimposed over said absorbent wadding layer so as to allow the transmittal of moisture therethrough to said moisture absorbent layer, said permeable inner sheet being affixed by connecting means to said moisture absorbent wadding;

d. two closely spaced electrical conductors extending across said diaper, positioned between said wadding layer and said permeable inner sheet; said conductors being affixed to said permeable inner sheet by securing means; and e. barrier means between said conductors so as to normally provide electrical isolation, but allowing an electrical short circuit between said conductors in the presence of an electrically conductive fluid.

17. An electrical moisture sensing diaper comprising in combination:

a. a moisture impervious backing sheet;

b. a layer of moisture absorbent wadding adjacent to and touching said backing sheet;

c. a non-absorbing moisture permeable inner sheet superimposed over said absorbent wadding so as to allow the transmittal of moisture through said permeable backing sheet to said wadding;

d. two closely spaced electrical conductors extending across said diaper positioned between said wadding layer and said backing sheet, said conductors being affixed to said backing sheet by securing means; and e. barrier means between said conductors so as to normally provide electrical isolation, but allowing an electrical short circuit between said conductors in the presence of an electrically conductive fluid.

18. A diaper as defined in claim 16 or 17 in which said barrier means comprises:

said backing sheet, said absorbent wadding layer and said permeable inner sheet being joined together at spaced intervals by securing means between said conductors so as to prevent contact between them when said diaper is folded or wrinkled, while allowing the transmittal of electrically conductive fluid from one conductor to the other through intervening passages between the joined spaced intervals, so that an electrical short circuit occurs between said conductors in the presence of said fluid.

19. In a dry absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing for superimposition over said inner sheet a non-absorbing digested liquid transmitting conductor bearing sheet adapted to substantially cover said absorbent wadding, b. said conductor bearing sheet defining one or more discrete prominence means on the surface to be superimposed over said inner sheet, c. said prominence means providing flow paths between succeeding prominence means, d. said prominence means extending from a first edge to a second edge opposite said first edge in an axial arrangement within a median location respective the edges of said surface to be superimposed, e. said prominence means providing attaching means for removably attaching said conductor bearing sheet to adjacent material, f. said prominence means defining to an affixed conductor bearing sheet a first and a second longitudinal conduit of circuitry located at the common touching comprising said inner sheet with conductor bearing sheet portions of said conductor bearing sheet not similarly adjoined at said prominence means, g. said conductor bearing sheet providing a second conductor removed from a first conductor, h. said prominence means including a removable covering strip covering said conductors and said attaching means, said strip being adapted to be removed before said conductor bearing sheet is affixed against the inner surface of a diaper, i. said first and said second conductor arranged to extend across and affixed by securing means to said prominence means bearing surface characterized by j. said first conductor being common to said touching comprising said first longitudinal conduit of circuitry, and k. said second conductor being common to said touching comprising said second longitudinal conduit of circuitry thereby normally providing electrical isolation between said first and said second conductor and prevent contact between them when the diaper is folded or wrinkled, but allowing an electrical short circuit in the presence of electrically conductive digested liquid draining into said absorbent wadding.

20. A combination as defined in claim 19, in which said attaching means consist of an adhesive.

21. A combination as defined in claim 20, wherein said attaching means are removably secured to adjacent material.

22. A combination as defined in claim 19, wherein said first and said second conductor consist of a tacky electrically conductive adhesive.

23. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said backing sheet one or more dimple depressing means to adjoin said securing means with said inner sheet and with said backing sheet within a median location respective the edges of said absorbent wadding, b. said dimple means defining flow paths to portions of said absorbent wadding not adjoined with said dimple means, c. said dimple means defining a first and a second longitudinal conduit of circuitry at the common touching comprising said absorbent wadding with backing sheet portions of said backing sheet nor similarly adjoined with said dimple means, d. by providing one conductor to register the feature of diaper soilage, e. said conductor superimposed over and affixed by securing means to the surface of said backing sheet facing said inner sheet, f. said conductor arranged to extend in the appearance of a horseshoe from a first edge of said backing sheet to a second edge opposite said first edge and slewed back to said first edge characterized by g. a portion of said extension from said first edge to said second edge being common to said touching comprising said first longitudinal conduit of circuitry, and h. a portion of said extension reflecting from said second edge to said first edge being common to said touching comprising said second longitudinal conduit of circuitry thereby normally providing electrical isolation between said portions of conductor and prevent contact between them when the diaper is folded or wrinkled, but allowing said continuous electrical circuit in an appropriately connected signaling means to indicate digestion recognition drained into the diaper.

24. A diaper which includes:
a. a first moisture permeable sheet;
b. two closely spaced electrical conductors extending across said first moisture permeable sheet;
c. a second moisture permeable sheet superimposed over and touching said first moisture permeable sheet and the two electrical conductors;
d. said first moisture permeable sheet, said two electrical conductors and said second moisture permeable sheet being joined together and the first moisture permeable sheet and the second moisture permeable sheet with the two electrical conductors thereinbetween being forced into each other in a corrugated pattern at spaced intervals by securing means between said two electrical conductors and the first moisture permeable sheet and the second moisture permeable sheet so as to prevent contact between the electrical conductors when said joined moisture permeable sheets is folded or wrinkled, while allowing the transmittal of electrically conductive fluid from one conductor to the other conductor, so that an electrical short circuit occurs between said conductors in the presence of said fluid; and
e. connecting means and removable covering strip covering said connecting means.

25. A combination as defined in claim 24, in which the conductor supporting material is affixed by securing means to other parts of a diaper.

26. A combination as defined in claim 25, in which a diaper is a disposable diaper.

27. A combination as defined in claim 26, characterized by an absorbent wadding layer substantially dimensioned as a diaper encapsulated between a moisture impervious backing sheet having an open surface and one non-absorbent inner sheet comprising one or more liquid pervious layers adjoined to form a single conductor supporting material.

28. A combination as defined in claim 27, in which the pattern locking the conductors in position is just wide enough to affix the conductors secured from displacement.

29. A combination as defined in claim 28, in which one or more sheets providing the conductor supporting material comprises a flexible strip just wide enough to support the conductors in a locked position.

30. A combination as defined in claim 25, in which the conductor supporting material is superimposed over an absorbent wadding layer comprising a part of a diaper so as to allow the transmittal of digested moisture through the conductor supporting material to the absorbent wadding layer.

31. A combination as defined in claim 30, in which securing means affix an absorbent wadding layer comprising a part of a diaper to the conductor supporting material.

32. A combination as defined in claim 31, in which a moisture transmitting sheet comprises a part of an absorbent wadding layer.

33. A combination as defined in claim 31, in which the conductor supporting material is separated from contact with an absorbent wadding layer comprising a part of a diaper by a moisture transmitting sheet.

34. A combination as defined in claim 33, in which a moisture transmitting sheet comprises a part of a diaper.

35. A combination as defined in claim 34, in which a moisture impervious backing sheet comprises a part of a diaper.

36. A combination as defined in claim 25, in which the conductor supporting material is affixed by securing means to a moisture impervious backing sheet comprising a part of a diaper.

37. A combination as defined in claim 36, in which an absorbent wadding layer is intermediate a moisture impervious backing sheet comprising a part of a diaper and the conductor supporting material.

38. A combination as defined in claim 37, in which a moisture transmitting sheet separates an absorbent wadding layer comprising a part of a diaper and the conductor supporting material.

39. A combination as defined in claim 38, in which a moisture transmitting sheet comprises a part of a diaper.

40. A diaper which includes:
 a. a moisture transmitting flexible support sheet;
 b. a fold in said moisture transmitting flexible support sheet along the central axis thereof, to provide a conductor layer sheet and a conductor cover sheet from said single moisture transmitting flexible support sheet;
 c. a pair of flexible conductors positioned between the conductor layer sheet and the folded over upon itself conductor cover sheet portion of said moisture transmitting flexible support sheet;
 d. securing means to prevent the flexible conductors from displacement and to prevent the folded over conductor cover sheet portion of said moisture transmitting flexible support sheet from inadvertently separating from the conductor layer sheet portion of said moisture transmitting flexible support sheet when folded or wrinkled or in the presence of electrically conductive fluid;
 e. connecting means and removable covering strip covering said connecting means.

41. A combination as defined in claim 40, the further modification in which said flexible support sheet providing said conductor layer sheet and said conductor cover sheet comprises of a flexible support strip to provide the conductor bearing material.

42. A combination as defined in claim 41, in which the flexible support sheet is a flexible strip for use with a diaper.

43. A combination as defined in claim 42, in which the flexible strip is provided just wide enough to support the conductors in a retained position.

44. A combination as defined in claim 43, in which the flexible strip is an integral part of a layer of a diaper means.

45. A combination as defined in claim 42, in which a diaper comprises a disposable diaper characterized by an absorbent wadding layer substantially dimensioned as a diaper encapsulated between a moisture impervious backing sheet having an open surface and one or more liquid pervious inner sheets.

46. A combination as defined in claim 42, in which the flexible strip is affixed by securing means to other parts comprising a diaper.

47. A combination as defined in claim 46, in which securing means affix the flexible strip intermediate the parts comprising a diaper.

48. A combination as defined in claim 47, in which a diaper means provides securing means to affix the flexible strip.

49. A combination as defined in claim 40, in which bonding means adjoin the conductor layer sheet and conductor cover sheet to secure the conductor bearing material.

50. A combination as defined in claim 40, in which means are provided for attaching one or more conductors to the surface which is common to each of the two sheets when folded over.

51. A combination as defined in claim 50, in which said attaching means is secured to the surface of one sheet which is common to the surface of the opposite sheet when folded over.

52. A combination as defined in claim 50, in which said attaching means is provided in discrete striped portions.

53. A combination as defined in claim 50, in which said attaching means is an adhesive means.

54. A combination as defined in claim 40, in which the conductor bearing material is affixed by securing means to other parts of a diaper.

55. A combination as defined in claim 54, in which a diaper is a disposable diaper.

56. A combination as defined in claim 55, characterized by an absorbent wadding layer substantially dimensioned as a diaper encapsulated between a moisture impervious backing sheet having an open surface and a non-absorbent inner sheet comprising a single liquid transmitting conductor bearing material of two parts wherein a fold in the conductor bearing material provides a second edge part superimposed over a first edge part to provide the inner sheet.

57. A combination as defined in claim 56, in which the securing means retaining the conductors positioned inbetween the folded conductor bearing material is just wide enough to secure the conductors.

58. A combination as defined in claim 54, in which the conductor bearing material is superimposed over an absorbent wadding layer comprising a part of a diaper so as to allow the transmittal of digested moisture through the conductor bearing material to the ansorbent wadding.

59. A combination as defined in claim 58, in which securing means affix an absorbent wadding layer comprising a part of a diaper to the conductor bearing material.

60. A combination as defined in claim 59, in which a moisture transmitting sheet comprises a part of an absorbent wadding layer.

61. A combination as defined in claim 59, in which the conductor bearing material is separated from contact with an absorbent wadding layer comprising a part of a diaper by a moisture transmitting sheet.

62. A combination as defined in claim 61, in which a moisture transmitting sheet comprises a part of a diaper.

63. A combination as defined in claim 62, in which a moisture impervious backing sheet comprises a part of a diaper.

64. A combination as defined in claim 54, in which the conductor bearing material is affixed by securing means to a moisture impervious backing sheet comprising a part of a diaper.

65. A combination as defined in claim 64, in which an absorbent wadding layer is intermediate a moisture impervious backing sheet comprising a part of a diaper and the conductor bearing material.

66. A combination as defined in claim 65, in which a moisture transmitting sheet separates an absorbent wadding layer comprising a part of a diaper and the conductor bearing material.

67. A combination as defined in claim 66, in which a moisture transmitting sheet comprises a part of a diaper.

68. A conductor strip for use in a diaper which includes:
 a. a first moisture permeable sheet;
 b. two closely spaced electrical conductors extending across said first moisture permeable sheet;
 c. a second moisture permeable sheet superimposed over and touching said first moisture permeable sheet and the two electrical conductors;
 d. said first and second moisture permeable sheets comprising a first and second flexible support strip to provide the conductor supporting material;
 e. said first moisture permeable sheet, said two electrical conductors and said second moisture permeable sheet being joined together and the first moisture permeable sheet and the second moisture permeable sheet with the two electrical conductors thereinbetween being forced into each other in a corrugated pattern at spaced intervals by securing means between said two electrical conductors and the first moisture permeable sheet and the second moisture permeable sheet so as to prevent contact between the electrical conductors when said joined moisture permeable sheets is folded or wrinkled, while allowing the transmittal of electrically conductive fluid from one conductor to the other conductor, so that an electrical short circuit occurs between said conductors in the presence of said fluid.

69. A combination as defined in claim 24 or 68 in which the conductor supporting material is a flexible strip for use with a diaper.

70. A combination as defined in claim 69, in which the flexible strip is provided just wide enough to support the conductors in a locked position.

71. A combination as defined in claim 70, in which the flexible strip is an integral part of a layer of a diaper means.

72. A combination as defined in claim 69, in which a diaper comprises a disposable diaper characterized by an absorbent wadding layer substantially dimensioned as a diaper encapsulated between a moisture impervious backing sheet having an open surface and one or more liquid pervious inner sheets.

73. A combination as defined in claim 69, in which the flexible strip is affixed by securing means to other parts comprising a diaper.

74. A combination as defined in claim 73, in which securing means affix the flexible strip intermediate the parts comprising a diaper.

75. A combination as defined in claim 74, in which a diaper means provides securing means to affix the flexible strip.

76. A combination as defined in claim 24 or 68, in which bonding means adjoin the moisture permeable sheets to affix the conductor supporting material.

77. A combination as defined in claim 24 or 68, in which means are provided for attaching one or more conductors to each of the moisture permeable sheet surfaces which contacts with the other.

78. A combination as defined in claim 77, in which said attaching means is secured to one surface which contacts with the other.

79. A combination as defined in claim 77, in which said attaching means is an adhesive means.

80. A combination as defined in claim 24 or 68, in which the common touching by opposite surfaces of the moisture permeable sheets with the conductors is adjoined by bonding means affixed at the touching.

81. In an absorbent wadding substantially dimensioned as a disposable diaper encapsulated between a moisture impervious backing sheet having an open surface and a non-absorbing moisture permeable inner sheet,
 the improvement of electrically sensing when said absorbent wadding requires the disposal of a soiled diaper
 a. by providing said backing sheet one strengthened and thickened longitudinal means within a median location respective the edges of said absorbent wadding,
 b. said strengthened and thickened means extending from a first edge to a second edge opposite said first edge,
 c. said strengthened and thickened means providing a first and a second longitudinal conduit of circuitry at the common touching comprising said absorbent wadding with backing sheet portions of said backing sheet not similarly provided with said strengthened and thickened means,
 d. by providing a second conductor removed from a first conductor,
 e. said first and said second conductor arranged to extend across and affixed by securing means to the surface of said backing sheet touching said absorbent wadding characterized by
 f. a portion of said first conductor being common to said touching comprising said first longitudinal conduit of circuitry, and
 g. a portion of said second conductor being common to said touching comprising said second longitudinal conduit of circuitry,
 to provide a torsion resistant means at the distance said second conductor is removed from said first conductor to prevent contact between them when the diaper is folded or wrinkled, but allowing an electrical short circuit in the presence of electrically conductive digested moisture draining into said absorbent wadding.

82. A diaper as defined in claim 4 or 81, in which said strengthened and thickened means provided said conductor supporting sheet comprises one or more folded panels at the distance either of two conductor lengths is removed from the other.

83. A diaper as defined in claim 4 or 81, in which said conductors are separated from contact with said absorbent wadding by a moisture transmitting sheet.

84. A combination as defined in claim 4 or 81, in which the conductor supporting sheet and said strengthened and thickened means comprise
   a. at least a first longitudinal fold,
   b. further folded away from said first fold back upon said first fold to define a second longitudinal fold,
   c. said folded portions of said sheet being affixed to itself by securing means.

85. A combination as defined in claims 4 or 81, in which said conductor supporting sheet comprises a flexible conductor supporting strip.

86. A combination as defined in claim 85, in which the parallel edges of the flexible conductor supporting strip are just wide enough to support said conductors.

87. A combination as defined in claim 86, in which the flexible conductor supporting strip is an integral part of a layer of a diaper means.

88. A diaper as defined in claim 4 or 81, in which the conductor supporting sheet is removably secured to the diaper.

89. A combination as defined in claim 88, in which a diaper comprises a disposable diaper characterized by an absorbent wadding layer substantially dimensioned as a diaper encapsulated between a moisture impervious backing sheet having an open surface and one or more liquid pervious inner sheets.

90. A combination as defined in claim 89, in which the flexible conductor supporting strip is affixed by securing means to other parts comprising a diaper.

91. A combination as defined in claim 90, in which securing means affix the flexible conductor supporting strip intermediate the parts comprising a diaper.

92. A combination as defined in claim 91, in which a diaper means provides securing means to affix the flexible conductor supporting strip.

93. A combination as defined in claim 90, in which means are provided said strengthened and thickened means for removably securing the strip with other elements comprising a diaper.

94. A combination as defined in claims 24 or 68 or 40 or 4 or 81 or 5 or 1 or 3 or 19, wherein a connecting means electrically adjoins the ends of said first and said second conductor extension opposite the conductor ends which connect into the circuit of an appropriately connected signaling means.

95. A combination as defined in claim 94, wherein said connecting means is the material comprising one of said conductors.

96. A combination as defined in claim 95, wherein said conductor means comprises an electrically conducting means provided with projections for gripping across the ends of two conductors; and
   easily bent over upon itself along one or more provided crease means for removably securing to conductor bearing material.

97. A combination as defined in claim 94, wherein said connecting means comprises a conductor means removably affixed to the ends of said first and said second conductor.

98. A combination as defined in claims 24 or 68 or 40 or 4 or 81 or 5 or 1 or 3 or 19, wherein said first and said second conductor consist of an electrically conductive adhesive means.

99. A combination as defined in claims 24 or 68 or 30 or 4 or 81 or 5 or 1 or 3 or 19, wherein said first and said second conductor is altered with electrical passivating means.

100. A combination as defined in claim 19, wherein only one of either of said conductors is altered.

101. In an absorbent wadding substantially dimensioned as a disposable diaper encapsulated between a moisture impervious backing sheet having an open surface and a non-absorbing moisture permeable inner sheet,
   the improvement of electrically sensing when said absorbent wadding requires the disposal of a soiled diaper
   a. by providing said backing sheet one or more dimple means to adjoin by securing means said inner sheet with said backing sheet within a median location respective the edges of said absorbent wadding,
   b. said dimple means providing flow paths to portions of said absorbent wadding not adjoined with said dimple means,
   c. said dimple means providing a first and a second longitudinal conduit of circuitry at the common touching comprising said inner sheet with backing sheet portions of said backing sheet not similarly adjoined with said dimple means,
   d. by providing a second conductor removed from a first conductor,
   e. said first and said second conductor arranged to extend across and affixed by securing means to the surface of said backing sheet facing said inner sheet characterized by
   f. a portion of said first conductor being common to said touching comprising said first longitudinal conduit of circuitry, and
   g. a portion of said second conductor being common to said touching comprising said second longitudinal conduit of circuitry
   thereby normally providing electrical isolation between said first and said second conductor and prevent contact between them when the diaper is folded or wrinkled, but allowing an electrical short circuit in the presence of electrically conductive moisture draining into said absorbent wadding.

102. In an absorbent wadding substantially dimensioned as a disposable diaper encapsulated between a moisture impervious backing sheet having an open surface and a non-absorbing moisture permeable inner sheet,
   the improvement of electrically sensing when said absorbent wadding requires the disposal of a soiled diaper
   a. by providing said backing sheet one or more dimple means to adjoin by securing means said absorbent wadding with said backing sheet within a median location respective the edges of said absorbent wadding,
   b. said dimple means providing flow paths to portions of said absorbent wadding not adjoined with said dimple means,
   c. said dimple means providing a first and a second longitudinal conduit of circuitry at the common touching comprising said absorbent wadding with backing sheet portions of said backing sheet not similarly adjoined with said dimple securing means,
   d. by providing a second conductor removed from a first conductor,
   e. said first and said second conductor arranged to extend across and affixed by securing means to the surface of said backing sheet facing said inner sheet characterized by f. a portion of said first conductor being common to said touching comprising said first longitudinal conduit of circuitry, and
g. a portion of said second conductor being common to said touching comprising said second longitudinal conduit of circuitry thereby normally providing electrical isolation between said first and said second conductor and prevent contact between them when the diaper is folded or wrinkled, but allowing an electrical short circuit in the presence of electrically conductive digested fluid draining into said absorbent wadding.

103. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said inner sheet one or more dimple securing means to adjoin by depressed means said backing sheet with said inner sheet within a median location respective the edges of said absorbent wadding,
b. said dimple securing means providing flow paths to portions of said absorbent wadding not adjoined with said dimple means,
c. said dimple means providing a first and a second longitudinal conduit of circuitry at the common touching comprising said backing sheet with inner sheet portions of said inner sheet not similarly adjoined with said dimple securing means,
d. by providing a second conductor removed from a first conductor,
e. said first and said second conductor arranged to extend across and affixed by securing means to the surface of said backing sheet facing said inner sheet characterized by
f. a portion of said first conductor being common to said touching comprising said first longitudinal conduit of circuitry, and
g. a portion of said second conductor being common to said touching comprising said second longitudinal conduit of circuitry thereby normally providing electrical isolation between said first and said second conductor and prevent contact between them when the diaper is folded or wrinkled, but allowing an electrical short circuit in the presence of electrically conductive digested moisture draining into said absorbent wadding.

104. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said inner sheet one or more dimple means within a median location respective the edges of said absorbent wadding,
b. said dimple means being depressed into said absorbent wadding to adjoin by securing means said backing sheet with said inner sheet,
c. a portion of said absorbent wadding being adjoined with said dimple means joining said backing sheet with said inner sheet,
d. said dimple means providing flow paths to portions of said absorbent wadding not adjoined with said dimple means,
e. said dimple means providing a first and a second longitudinal conduit of circuitry at the common touching comprising said absorbent wadding with backing sheet portions of said backing sheet not similarly adjoined with said dimple means,
f. by providing a second conductor removed from a first conductor,
g. said first and said second conductor arranged to extend across and affixed by securing means to the surface of said backing sheet facing said inner sheet characterized by
h. a portion of said first conductor being common to said touching comprising said first longitudinal conduit of circuitry, and
i. a portion of said second conductor being common to said touching comprising said second longitudinal conduit of circuitry thereby normally providing electrical isolation between said first and said second conductor and prevent contact between them when the diaper is folded or wrinkled, but allowing an electrical short circuit in the presence of electrically conductive digested liquid draining into said absorbent wadding.

105. A diaper as defined in claim 1 or 2 or 101 or 102 or 103 or 104, in which said first and said second conductor are affixed by securing means to a flexible conductor supporting strip which at the distance said second conductor is removed from said first conductor in turn is affixed intermediate the touching comprising the parts adjoined with said dimple securing means characterized by a. a portion of said first conductor being common to said touching comprising said first longitudinal conduit of circuitry, and
b. a portion of said second conductor being common to said touching comprising said second longitudinal conduit of circuitry.

106. A diaper as defined in claim 1 or 2 or 81 or 101 or 102 or 103 or 104, in which said conductors are separated from contact with said moisture absorbent wadding layer by a moisture transmitting sheet.

107. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said backing sheet one or more dimple depressing means to adjoin said securing means within a median location respective the edges of said absorbent wadding,
b. said dimple means being depressed into said absorbent wadding by securing means to adjoin said securing means with said inner sheet and with said backing sheet, c. a portion of said absorbent wadding being adjoined with said dimple securing means joining said inner sheet with said backing sheet, d. said dimple securing means defining flow paths to portions of said absorbent wadding not adjoined with said dimple securing means, e. said dimple securing means providing a first and a second longitudinal conduit of circuitry at the common touching comprising said absorbent wadding with inner sheet portions of said inner sheet not similarly adjoined with said dimple securing means, f. by providing a second conductor removed from a first conductor, g. said first and said second conductor arranged to extend across and affixed by securing means to the surface of said inner sheet facing said backing sheet characterized by h. a portion of said first conductor being common to said touching comprising said first longitudinal conduit of circuitry, and i. a portion of said second conductor being common to said touching comprising said second longitudinal conduit of circuitry thereby normally providing electrical isolation between said first and said second conductor and prevent contact between them when the diaper is folded or wrinkled, but allowing an electrical short circuit in the presence of electrically conductive digested liquid draining into said absorbent wadding.

108. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said inner sheet one or more dimple securing means to adjoin by depressed means said backing sheet with said inner sheet within a median location respective the edges of said absorbent wadding, b. said dimple means providing flow paths to portions of said absorbent wadding not adjoined with said dimple means, c. said dimple means defining a first and a second longitudinal conduit of circuitry at the common touching comprising said backing sheet with inner sheet portions of said inner sheet not similarly adjoined with said dimple securing means, d. by providing a second conductor removed from a first conductor, e. said first and said second conductor arranged to extend across and affixed by securing means to the surface of said inner sheet facing said backing sheet characterized by f. a portion of said first conductor being common to said touching comprising said first longitudinal conduit of circuitry, and g. a portion of said second conductor being common to said touching comprising said second longitudinal conduit of circuitry thereby normally providing electrical isolation between said first and said second conductor and prevent contact between them when the diaper is folded or wrinkled, but allowing an electrical short circuit in the presence of electrically conductive digested fluid draining into said absorbent wadding.

109. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said backing sheet one or more dimple securing means to adjoin by depressed means said inner sheet with said backing sheet within a median location respective the edges of said absorbent wadding, b. said dimple securing means defining flow paths to portions of said absorbent wadding not adjoined with said dimple means, c. said dimple means providing a first and a second longitudinal conduit of circuitry at the common touching comprising said inner sheet with backing sheet portions of said backing sheet not similarly adjoined with said dimple securing means, d. by providing a second conductor removed from a first conductor, e. said first and said second conductor arranged to extend across and affixed by securing means to the surface of said inner sheet facing said backing sheet characterized by f. a portion of said first conductor being common to said touching comprising said first longitudinal conduit of circuitry, and g. a portion of said second conductor being common to said touching comprising said second longitudinal conduit of circuitry thereby normally providing electrical isolation between said first and said second conductor and prevent contact between them when the diaper is folded or wrinkled, but allowing an electrical short circuit in the presence of electrically conductive digested moisture draining into said absorbent wadding.

110. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said inner sheet one or more dimple depressing means to adjoin said securing means with said backing sheet and with said inner sheet within a median location respective the edges of said absorbent wadding, b. said dimple means defining flow paths to portions of said absorbent wadding not adjoined with said securing means, c. said dimple means providing a first and a second longitudinal conduit of circuitry at the common touching comprising said absorbent wadding and inner sheet portions of said inner sheet not similarly adjoined with said dimple means, d. by providing a second conductor removed from a first conductor, e. said first and said second conductor arranged to extend across and affixed by securing means to the surface of said inner sheet facing said backing sheet characterized by f. a portion of said first conductor being common to said touching comprising said first longitudinal conduit of circuitry, and g. a portion of said second conductor being common to said touching comprising said second longitudinal conduit of circuitry thereby normally providing electrical isolation between said first and said second conductor and prevent contact between them when the diaper is folded or wrinkled, but allowing an electrical short circuit in the presence of electrically conductive digested liquid emptying into said absorbent wadding.

111. In a dry absorbent wadding substantially dimensioned as a disposable diaper encapsulated between a moisture impervious backing sheet having an open surface and a non-absorbing moisture permeable inner sheet provided with a coextensive layer separating said backing sheet and said absorbent wadding, the improvement of electrically sensing when said absorbent wadding requires the disposal of a soiled diaper a. by providing said inner sheet one or more dimple depressing means to adjoin said securing means with said absorbent wadding and with said layer separating said backing sheet and said absorbent wadding within a median location respective the edges of said absorbent wadding, b. said dimple means defining flow paths to portions of said absorbent wadding not adjoined with said securing means, c. said dimple means defining a first and a second longitudinal conduit of circuitry at the common touching comprising said absorbent wadding with inner sheet portions of said inner sheet not similarly adjoined with said dimple securing means, d. by providing a second conductor removed from a first conductor, e. said first and said second conductor arranged to extend across and affixed by securing means to the surface of said inner sheet facing said layer separating said backing sheet and said absorbent wadding characterized by f. a portion of said first conductor being common to said touching comprising said first longitudinal conduit of circuitry, and g. a portion of said second conductor being common to said touching comprising said second longitudinal conduit of circuitry thereby normally providing electrical isolation between said first and said second conductor and prevent contact between them when the diaper is folded or wrinkled, but allowing an electrical short circuit in the presence of electrically conductive digested fluid draining into said absorbent wadding.

112. In a dry absorbent wadding substantially dimensioned as a disposable diaper encapsulated between a moisture impervious backing sheet having an open surface and a non-absorbing moisture permeable inner sheet provided with a coextensive layer separating said backing sheet and said absorbent wadding, the improvement of electrically sensing when said absorbent wadding requires the disposal of a soiled diaper a. by providing said inner sheet one or more dimple depressing means to adjoin said securing means with said absorbent wadding and with said layer separating said backing sheet and said absorbent wadding within a median location respective the edges of said absorbent wadding, b. said dimple means defining flow paths to portions of said absorbent wadding not adjoined with said securing means, c. said dimple means defining a first and a second longitudinal conduit of circuitry at the common touching comprising said absorbent wadding with separating layer portions of said separating layer not similarly adjoined with said dimple securing means, d. by providing a second conductor removed from a first conductor, e. said first and said second conductor arranged to extend across and affixed by securing means to said separating layer characterized by f. a portion of said first conductor being common to the separating layer comprising the first longitudinal conduit of circuitry, and g. a portion of said second conductor being common to the separating layer comprising the second longitudinal conduit of circuitry thereby normally providing electrical isolation between said first and said second conductor and prevent contact between them when the diaper is folded or wrinkled, but allowing an electrical short circuit in the presence of electrically conductive digested fluid draining into said absorbent wadding.

113. A diaper as defined in claim 3 or 107 or 108 or 109 or 110 or 111 or 112, in which said first and said second conductor are affixed by securing means to a flexible conductor supporting strip which at the distance said second conductor is removed from said first conductor in turn is affixed intermediate the touching comprising the parts adjoined with said dimple securing means characterized by a. a portion of said first conductor being common to said touching comprising said first longitudinal conduit of circuitry, and b. a portion of said second conductor being common to said touching comprising said second longitudinal conduit of circuitry.

114. A diaper as definined in claim 3 or 107 or 108 or 109 or 110 or 111 or 112, in which said conductors are separated from contact with said moisture absorbent wadding layer by a moisture transmitting sheet.

115. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said inner sheet one or more dimple depressing means to adjoin said securing means with said backing sheet and with said inner sheet within a median location respective the edges of said absorbent wadding, b. said dimple means defining flow paths to portions of said absorbent wadding not adjoined with said dimple means, c. said dimple means defining a first and a second longitudinal conduit of circuitry at the common touching comprising said absorbent wadding with backing sheet portions of said backing sheet not similarly adjoined with said dimple means, d. by providing one conductor to register the feature of diaper soilage, e. said conductor superimposed over and affixed by securing means to the surface of said backing sheet facing said inner sheet, f. said conductor arranged to extend in the appearance of a horseshoe from a first edge of said backing sheet to a second edge opposite said first edge and slewed back to said first edge characterized by g. a portion of said extension from said first edge to said second edge being common to said touching comprising said first longitudinal conduit of circuitry, and h. a portion of said extension reflecting from said second edge to said first edge being common to said touching comprising said second longitudinal conduit of circuitry thereby normally providing electrical isolation between said portions of conductor and prevent contact between them when the diaper is folded or wrinkled, but allowing said continuous electrical circuit in an appropriately connected signaling means to indicate digestion recognition drained into the diaper.

116. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said backing sheet one or more dimple depressing means to adjoin said securing means with said inner sheet and with said backing sheet within a median location respective the edges of said absorbent wadding, b. said dimple means defining flow paths to portions of said absorbent wadding not adjoined with said dimple means, c. said dimple means defining a first and a second longitudinal conduit of circuitry at the common touching comprising said absorbent wadding with inner sheet portions of said inner sheet not similarly adjoined with said dimple means, d. by providing one conductor to register the feature of diaper soilage, e. said conductor superimposed over and affixed by securing means to the surface of said inner sheet facing said backing sheet, f. said conductor arranged to extend in the appearance of a horseshoe from a first edge of said backing sheet to a second edge opposite said first edge and slewed back to said first edge characterized by g. a portion of said extension from said first edge to said second edge being common to said touching comprising said first longitudinal conduit of circuitry, and h. a portion of said extension reflecting from said second edge to said first edge being common to said touching comprising said second longitudinal conduit of circuitry thereby normally providing electrical isolation between said portions of conductor and prevent contact between them when the diaper is folded or wrinkled, but allowing said continuous electrical circuit in an appropriately connected signaling means to indicate digestion recognition drained into the diaper.

117. In a dry absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing for superimposition over said inner sheet a non-absorbing digested liquid transmitting conductor bearing sheet adapted to substantially cover said absorbent wadding, b. said conductor bearing sheet defining one or more discrete prominence means on the surface to be superimposed over said inner sheet, c. said prominence means providing flow paths between succeeding prominence means, d. said prominence means extending from a first edge to a second edge opposite said first edge in an axial arrangement within a median location respective the edges of said surface to be superimposed, e. said prominence means providing attaching means for removably attaching said conductor bearing sheet to adjacent material, f. said prominence means defining in an affixed conductor bearing sheet a first and a second longitudinal conduit of circuitry located at the common touching comprising said inner sheet with conductor bearing sheet portions of said conductor bearing sheet not similarly adjoined at said prominence means, g. said conductor bearing sheet providing one conductor to register the feature of diaper soilage, h. said prominence means including a removable covering strip covering said conductors and said attaching means, said strip being adapted to be removed before said conductor bearing sheet is affixed against the inner surface of a diaper, i. said conductor superimposed over and affixed by securing means to said prominence means bearing surface characterized by j. said conductor arranged to extend in the appearance of a horseshoe from a first edge of said conductor bearing sheet to a second edge opposite said first edge and slewed back to said first edge characterized by k. a portion of said extension from said first edge to said second edge being common to said touching comprising said first longitudinal conduit of circuitry, and l. a portion of said extension reflecting from said second edge to said first edge being common to said touching comprising said second longitudinal conduit of circuitry thereby normally providing electrical isolation between said portions of conductor and prevent contact between them when the diaper is folded or wrinkled, but allowing said continuous electrical circuit in an appropriately connected signaling means to indicate digestion recognition drained into the diaper.

118. A combination as defined in claim 117, wherein said attaching means consist of an adhesive means.

119. A combination as defined in claim 118, wherein said attaching means is removably secured to adjacent material.

120. In an absorbent wadding substantially dimensioned as a disposable diaper encapsulated between a moisture impervious backing sheet an open surface and a non-absorbing moisture permeable inner sheet,
 the improvement of electrically sensing when said absorbent wadding requires the disposal of a soiled diaper
 a. by providing said backing sheet one or more depressed means within a median location respective the edges of said absorbent wadding,
 b. said depressed means being dimpled into said absorbent wadding by securing means to adjoin said inner sheet with said backing sheet,
 c. a portion of said absorbent wadding being adjoined with said securing means joining said inner sheet with said backing sheet,
 d. said securing means defining flow paths to portions of said absorbent wadding not adjoined with said secured dimple means,
 e. said securing means providing a first and a second longitudinal conduit of circuitry at the common touching comprising said absorbent wadding with backing sheet portions of said backing sheet not similarly adjoined with said dimple means; and
 a first and a second longitudinal conduit of circuitry at the common touching comprising said absorbent wadding with inner sheet portions of said inner sheet not similarly adjoined with said dimple means,
 f. by providing one conductor to register the feature of diaper soilage,
 g. said conductor superimposed over and affixed by securing means to the surface of said backing sheet facing said inner sheet,
 h. said conductor arranged to extend in the appearance of a horseshoe from a first edge of said backing sheet to a second edge opposite said first edge and slewed back to said first edge characterized by
 i. a portion of said extension from said first edge to said second edge being common to said absorbent wadding and backing sheet touching comprising said first longitudinal conduit of circuitry, and
 j. a portion of said extension reflecting from said second edge to said first edge being common to said absorbent wadding and backing sheet touching comprising said second longitudinal conduit of circuitry
 thereby normally providing electrical isolation between said portions of conductor and prevent contact between them when the diaper is folded or wrinkled, but allowing said continuous electrical circuit in an appropriately connected signaling means to indicate digestion recognition drained into the diaper.

121. In an absorbent wadding substantially dimensioned as a disposable diaper encapsulated between a moisture impervious backing sheet having an open surface and a non-absorbing moisture permeable inner sheet,
 the improvement of electrically sensing when said absorbent wadding requires the disposal of a soiled diaper
 a. by providing said inner sheet one or more depressed means within a median location respective the edges of said absorbent wadding,
 b. said depressed means being dimpled into said absorbent wadding by securing means to adjoin said backing sheet with said inner sheet,
 c. a portion of said absorbent wadding being adjoined with said securing means joining said inner sheet with said backing sheet,
 d. said securing means defining flow paths to portions of said absorbent wadding not adjoined with said secured dimple means,
 e. said securing means providing a first and a second longitudinal conduit of circuitry at the common touching comprising said absorbent wadding with backing sheet portions of said backing sheet not similarly adjoined with said dimple means; and
 a first and a second longitudinal conduit of circuitry at the common touching comprising said absorbent wadding with inner sheet portions of said inner sheet not similarly adjoined with said dimple means,
 f. by providing one conductor to register the feature of diaper soilage,
 g. said conductor superimposed over and affixed by securing means to the surface of said backing sheet facing said inner sheet,
 h. said conductor arranged to extend in the appearance of a horseshoe from a first edge of said backing sheet to a second edge opposite said first edge and slewed back to said first edge characterized by
 i. a portion of said extension from said first edge to said second edge being common to said absorbent wadding and backing sheet touching comprising said first longitudinal conduit of circuitry, and
 j. a portion of said extension reflecting from said second edge to said first edge being common to said absorbent wadding and backing sheet touching comprising said second longitudinal conduit of circuitry
 thereby normally providing electrical isolation between said portions of conductor and prevent contact between them when the diaper is folded or wrinkled, but allowing said continuous electrical circuit in an appropriately connected signaling means to indicate digestion recognition drained into the diaper.

122. In an absorbent wadding substantially dimensioned as a disposable diaper encapsulated between a moisture impervious backing sheet having an open surface and a non-absorbing moisture permeable inner sheet.
 the improvement of electrically sensing when said absorbent wadding requires the disposal of a soiled diaper
 a. by providing said inner sheet one or more depressed means within a median location respective the edges of said absorbent wadding,
 b. said depressed means being dimpled into said absorbent wadding by securing means to adjoin said backing sheet with said inner sheet,
 c. a portion of said absorbent wadding being adjoined with said securing means joining said backing sheet with said inner sheet,
 d. said securing means defining flow paths to portions of said absorbent wadding not adjoined with said secured dimple means, e. said securing means providing a first and a second longitudinal conduit of circuitry at the common touching comprising said absorbent wadding with inner sheet portions of said inner sheet not similarly adjoined with said dimple means; and a first and a second longitudinal conduit of circuitry at the common touching comprising said absorbent wadding with backing sheet portions of said backing sheet not similarly adjoined with said dimple means, f. by providing one conductor to register the feature of diaper soilage, g. said conductor superimposed over and affixed by securing means to the surface of said inner sheet facing said backing sheet, h. said conductor arranged to extend in the appearance of a horseshoe from a first edge of said inner sheet to a second edge opposite said first edge and slewed back to said first edge characterized by i. a portion of said extension from said first edge to said second edge being common to said absorbent wadding and inner sheet touching comprising said first longitudinal conduit of circuitry, and j. a portion of said extension reflecting from said second edge to said first edge being common to said absorbent wadding and inner sheet touching comprising said second longitudinal conduit of circuitry thereby normally providing electrical isolation between said portions of conductor and prevent contact between them when the diaper is folded or wrinkled, but allowing said continuous electrical circuit in an appropriately connected signaling means to indicate digestion recognition drained into the diaper.

123. A combination as defined in claims 24 or 68 or 40 or 4 or 81 or 5 or 1 or 3 or 19 or 23 or 117 or 122, wherein indicator means comprise:

a signaling means which alters in its indication in accordance with changes of resistance in one length of an altered conductor means characterized wherein the phenomina acted by said signaling means relates to the distance said connected signaling means is removed from the location digested moisture electrically short circuits portions of length of said conductor means, thereby defining the nature of digested moisture within said absorbent wadding.

124. The diaper as defined in claims 24 or 68 or 40 or 4 or 81 or 5 or 1 or 3 or 19 or 23 or 117 or 122 in which there is a moisture delaying means coated to one or more of said conductors to protect against electrical short circuiting of the conductors by a negligible amount of moisture such as might occur due to perspiring in order to prevent false or erroneous signals.

125. A combination as defined in claims 24 or 68 or 40 or 4 or 81 or 5 or 1 or 3 or 23 or 117 or 122, in which there is a remotely located alarm means and in which said electrical conductors form an antenna for radiating a signal to said alarm means.

126. A combination as defined in claim 125, wherein a separate conductor affixed by securing means similar to said conductors forms an antenna for radiating a signal to said alarm means.

127. A combination as defined in claim 126, wherein said antenna conductor is affixed by securing means on the obverse surface of a conductor bearing material.

128. A combination as defined in claim 126, wherein said antenna conductor is affixed by securing means to an open surface comprising a part of a diaper.

129. A combination as defined in claims 23 or 117 or 122, wherein said conductor consists of an electrically conductive adhesive means.

130. A combination as defined in claims 23 or 117 or 122, wherein said conductor is altered with electrical passivating means.

131. A combination as defined in claims 23 or 117 or 122, wherein a portion of said one conductor consists of a removably affixed electrical connector means.

132. In an absorbent wadding substantially dimensioned as a disposable diaper encapsulated between a moisture impervious backing sheet having an open surface and a non-absorbing moisture permeable inner sheet, the improvement of electrically sensing when said absorbent wadding requires the disposal of a soiled diaper a. by providing said inner sheet one or more depressed means within a median location respective the edges of said absorbent wadding, b. said depressed means being dimpled into said absorbent wadding by securing means to adjoin said backing sheet with said inner sheet, c. a portion of said absorbent wadding being adjoined with said securing means joining said backing sheet with said inner sheet, d. said securing means defining flow paths to portions of said absorbent wadding not adjoined with said secured dimple means, e. said securing means providing a first and a second longitudinal conduit of circuitry at the common touching comprising said absorbent wadding with inner sheet portions of said inner sheet not similarly adjoined with said dimple means; and a first and a second longitudinal conduit of circuitry at the common touching comprising said absorbent wadding with backing sheet portions of said backing sheet not similarly adjoined with said dimple means, f. by providing one conductor comprising a first and a second part and a third removably secured part, g. said conductor arranged to extend in the appearance of a horseshoe from a first edge of the diaper to a second edge opposite said first edge and slewed from said second edge back to said first edge characterized by h. said first conductor part superimposed over and affixed by securing means to the surface of said inner sheet facing said backing sheet, i. said second conductor part superimposed over and affixed by securing means to the surface of said backing sheet facing said inner sheet; and j. slewing means comprising said third conductor part removably affixed to the ends of said first and said second conductor part opposite said conductor ends which connect into the circuitry of a signal means characterized by k. a portion of said extension from said first edge to said second edge being common to said absorbent wadding and inner sheet touching comprising said first longitudinal conduit of circuitry, and l. a portion of said extension reflecting from said second edge to said first edge being common to said absorbent wadding and inner sheet touching comprising said second longitudinal conduit of circuitry thereby normally providing electrical isolation between said portions of conductor and prevent contact between them when the diaper is folded or wrinkled, but allowing said continuous electrical circuit in an appropriately connected signaling means to indicate digestion recognition drained into the diaper.

133. A conductor strip for use in a diaper which includes:
 a. a moisture permeable strip means;
 b. an adhesive means provided said strip;
 c. two current-conveying means provided along the edges of said strip and forming a part of said adhesive means; and
 d. a layer of moisture distributing flocking means provided said strip assembly to prevent said current-conveying means from electrically short circuiting when said strip assembly touches adjacent means while allowing moisture to transfer across the surfaces of said strip assembly.

134. A combination as defined in claim 133, wherein said current-conveying means consist of an adhesive means.

135. A combination as defined in claim 133, wherein said moisture permeable strip means consists of a moisture impervious material.

136. The combination as defined in claim 133, in which said strip means is moisture impervious.

137. The combination as defined in claim 133, in which said adhesive means is removably secured to said moisture distributing flocking means provided said strip means.

* * * * *